(12) United States Patent
Robinson

(10) Patent No.: US 9,687,285 B2
(45) Date of Patent: Jun. 27, 2017

(54) FENESTRATED BONE SCREWS AND METHODS OF BONE FASTENING AND STABILIZATION

(71) Applicant: James C. Robinson, Atlanta, GA (US)

(72) Inventor: James C. Robinson, Atlanta, GA (US)

(73) Assignee: SPECTRUM SPINE IP HOLDINGS, LLC, Atlanta, GA (US)

( * ) Notice: Subject to any disclaimer, the term of this patent is extended or adjusted under 35 U.S.C. 154(b) by 0 days.

(21) Appl. No.: 14/181,647

(22) Filed: Feb. 15, 2014

(65) Prior Publication Data

US 2014/0236242 A1 Aug. 21, 2014

Related U.S. Application Data

(63) Continuation-in-part of application No. 13/358,169, filed on Jan. 25, 2012, now abandoned.

(60) Provisional application No. 61/794,441, filed on Mar. 15, 2013.

(51) Int. Cl.
| | |
|---|---|
| *A61B 17/70* | (2006.01) |
| *A61B 17/86* | (2006.01) |
| *A61B 17/88* | (2006.01) |
| *A61B 17/16* | (2006.01) |
| *A61B 90/00* | (2016.01) |

(52) U.S. Cl.
CPC ......... *A61B 17/864* (2013.01); *A61B 17/863* (2013.01); *A61B 17/8605* (2013.01); *A61B 17/8811* (2013.01); *A61B 17/8891* (2013.01); *A61B 17/1671* (2013.01); *A61B 17/8615* (2013.01); *A61B 2090/062* (2016.02)

(58) Field of Classification Search
CPC .............. A61B 17/864; A61B 17/8625; A61B 17/8635; A61B 17/8811; A61B 17/7098; A61B 17/3472; A61B 17/686
USPC .......................... 606/300–321, 323, 104, 92
See application file for complete search history.

(56) References Cited

U.S. PATENT DOCUMENTS

| | | | |
|---|---|---|---|
| 4,640,271 | A | 2/1987 | Lower |
| 5,725,581 | A | 3/1998 | Brånemark |
| 6,755,835 | B2 | 6/2004 | Schultheiss et al. |
| 7,608,062 | B2 | 10/2009 | Sweeney |
| 7,608,097 | B2 | 10/2009 | Kyle |
| 2001/0021852 | A1 | 9/2001 | Chappius |
| 2004/0225292 | A1 | 11/2004 | Sasso et al. |
| 2006/0085068 | A1 | 4/2006 | Barry |
| 2007/0276402 | A1 | 11/2007 | Frankel et al. |
| 2008/0147128 | A1 | 6/2008 | Fritzinger |
| 2008/0262555 | A1 | 10/2008 | Assell et al. |
| 2010/0211113 | A1 | 8/2010 | Olson et al. |
| 2011/0004256 | A1 | 1/2011 | Biedermann et al. |
| 2011/0060373 | A1 | 3/2011 | Russell et al. |

*Primary Examiner* — Eduardo C Robert
*Assistant Examiner* — Michelle C Eckman
(74) *Attorney, Agent, or Firm* — FisherBroyles, LLP; Anthony J. DoVale

(57) ABSTRACT

Systems, methods, and apparatuses for bone fixation are presented. In one aspect, presented herein is a screw for bone fixation, an insertion tool, and a method for stabilization across a bone joint of the spine. The bone screw has an elongate shank defining an internal longitudinal passage. The screw has an external threaded surface and a tapered distal end. The insertion tool engages the head of the screw and is used to drive the screw into the desired bone joint.

18 Claims, 28 Drawing Sheets

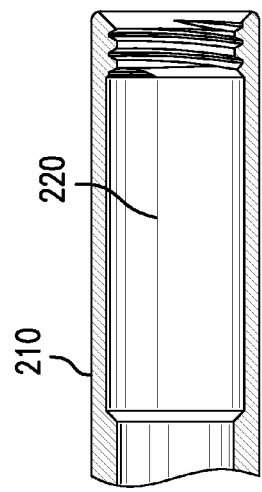
FIG. 19
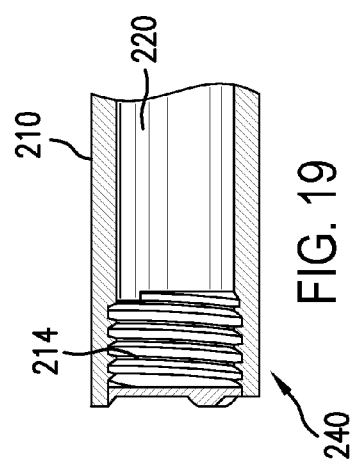
FIG. 20
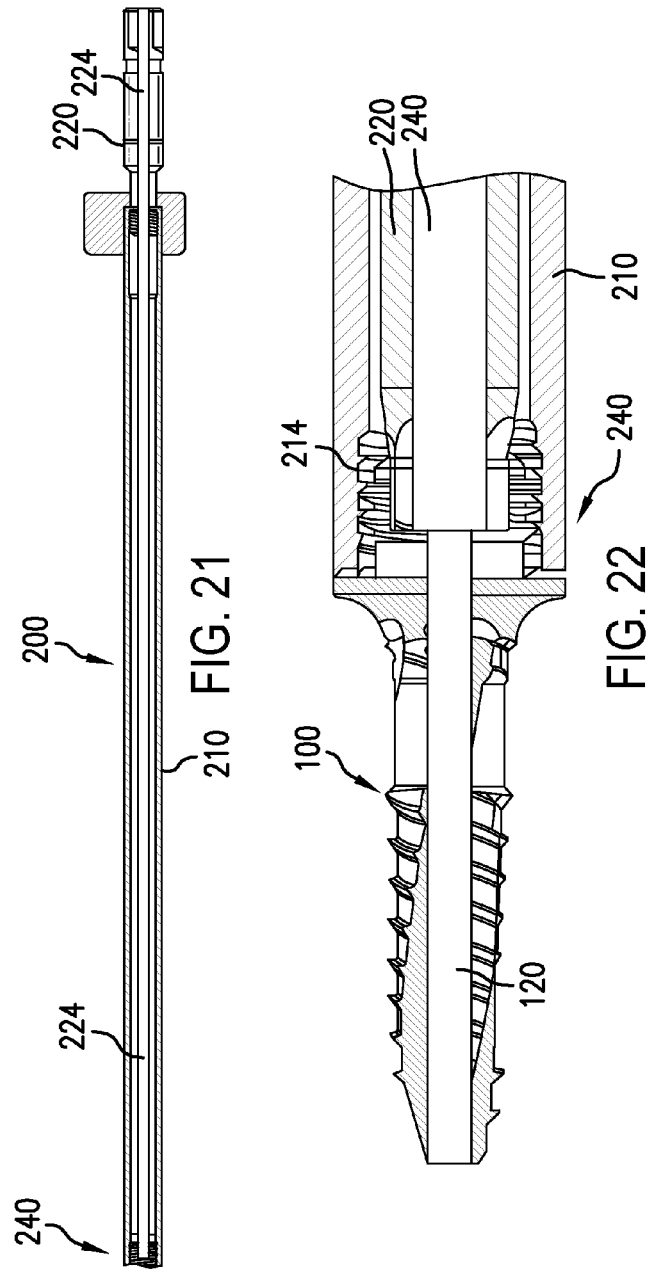
FIG. 21
FIG. 22

FENESTRATED BONE SCREWS AND METHODS OF BONE FASTENING AND STABILIZATION

CONTINUITY

The application claims priority to and is a continuation in part of pending U.S. application Ser. No. 13/358,169, filed on Jan. 25, 2012, and U.S. application Ser. No. 61/794,441, filed on Mar. 15, 2013, both of which are incorporated herein in their entirety.

BACKGROUND

The following disclosure relates generally to medical devices, systems and methods, including, for example, a bone screw system and a method of using it in surgery.

A variety of support assemblies currently exist which may be surgically implanted into a patient's intervertebral space so as to provide support between two (or more) adjacent vertebrae. Surgical implantation of such systems is typically used to provide support along the spinal column in cases where a portion of the patient's intervertebral anatomy has become diseased or destroyed. In addition, such support systems are also commonly used following a discectomy, wherein the patient's intervertebral disc is surgically removed.

Most commonly, existing support systems typically operate by inhibiting normal movement between the adjacent vertebrae, thereby holding these vertebrae at fixed positions relative to one another, with the mechanical body of the supporting structure providing the needed support along the patient's spinal column. Such supporting systems are typically made of stainless steel or titanium, and are designed to permanently remain within the patient's body.

It is beneficial, in addition to fixation, to try to stimulate bone growth between the adjacent vertebrae. To do so, spine surgeons use bone graft material in addition to fixation devices. Bone graft doesn't heal or fuse the spine immediately; instead, bone graft provides a foundation or scaffold for the patient's body to grow new bone. Bone graft can stimulate new bone production. When new bone grows and solidifies, fusion occurs. Although instrumentation (e.g., screws, rods) is often used for initial stabilization (postoperative), it is the healing of bone that welds vertebrae together to create long-term stability.

There are two general types of bone grafts: real bone and bone graft substitutes. Real bone can come from the patient (autograft) or from a donor bone (allograft). Also used in these types of surgery are bone substitute, osteoinductive agent, and bone cement. There is a need for alternative systems and methods that use both fixation and fusion.

SUMMARY

Presented herein are systems, methods, and apparatuses for bone fixation. In one aspect, presented herein is a screw for bone fixation. The bone screw, in an exemplified aspect, comprises an elongate shank defining an internal longitudinal passage. The screw has an external threaded surface and a tapered distal end.

Presented herein is also an insertion tool. The insertion tool comprises an elongate tube having a tube distal end configured to mate with a portion of the head of the screw and a drive rod disposed within the tube. In one aspect, the rod has a rod distal end configured to mate with and drive the screw. In one exemplary aspect, the rod defines a longitudinal drive rod passageway, wherein the rod is selectively removable from the elongate tube.

Also presented herein is a method for stabilization across a bone joint in the spine. The method comprises providing a bone screw, accessing a desired motion segment of the spine, driving the bone screw across the desired bone joint, and injecting bone graft material into the proximity of the bone joint.

Related methods of operation are also provided. Other apparatuses, methods, systems, features, and advantages of the location module will be or become apparent to one with skill in the art upon examination of the following figures and detailed description. It is intended that all such additional apparatuses, methods, systems, features, and advantages be included within this description, be within the scope of the bone screw system and method, and be protected by the accompanying claims.

BRIEF DESCRIPTION OF THE DRAWINGS

These and other features of the preferred embodiments of the present invention will become more apparent in the detailed description in which reference is made to the appended drawings wherein:

FIG. 19 is a partial cut-away side elevational view of a distal portion of the elongate tube of FIG. 17;

FIG. 20 is a partial cut-away side elevational view of a proximal portion of the elongate tube of FIG. 17;

FIG. 21 is a cut-away side elevational view of the insertion tool of FIG. 14, cut along line 21-21 of FIG. 15;

FIG. 22 is a partial cut-away side elevational view of a distal portion of the insertion tool of FIG. 14, showing the tool engaged with a bone screw;

Figure 23A:
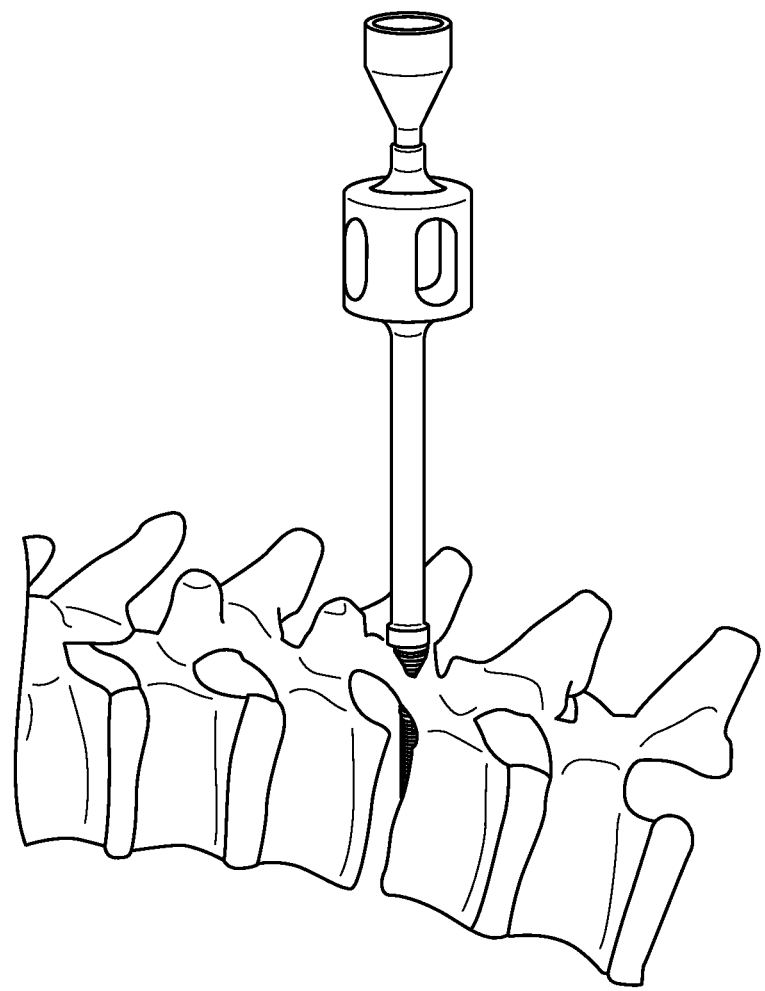
FIG. 23A is a perspective view of one aspect of a bone screw and an insertion tool for inserting a bone screw.
Figure 23C:
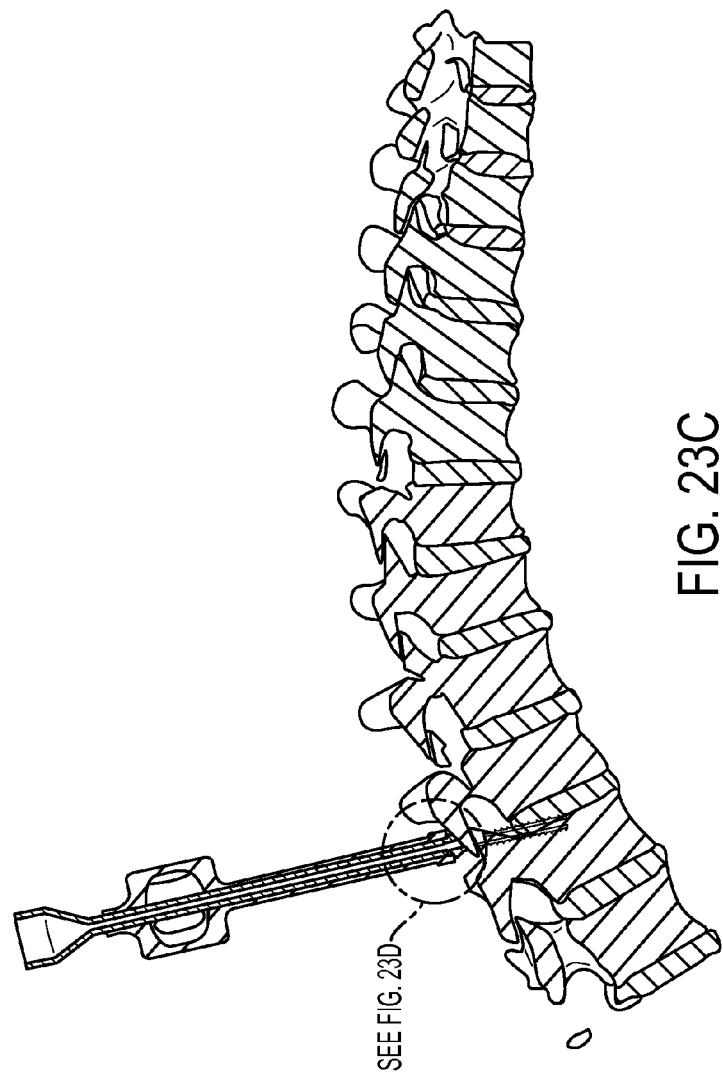
FIG. 23C is partial cut away side elevational view of the bone screw and insertion tool of FIG. 23A, cut along line 23C-23C of FIG. 23B.
Figure 23B:
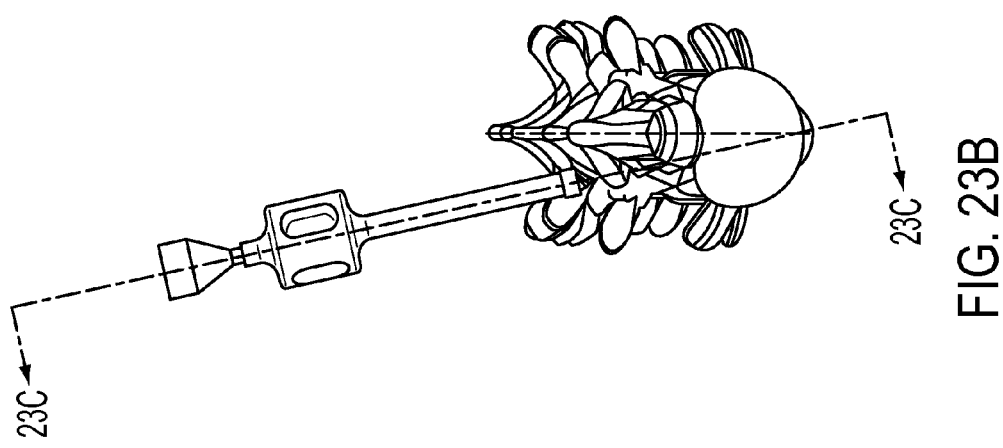
FIG. 23B is a front elevational view of the bone screw and insertion tool of FIG. 23A.
Figure 23D:
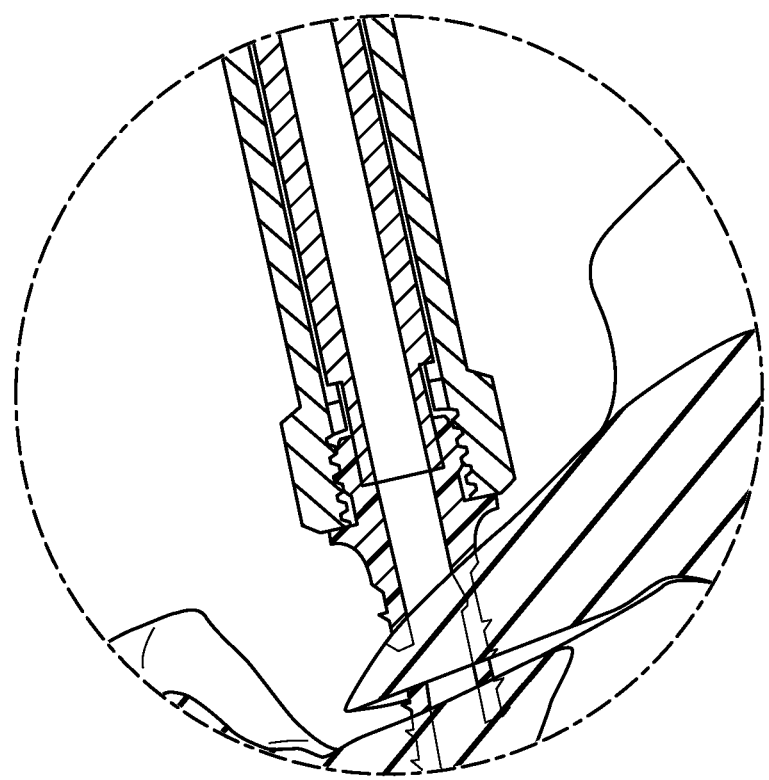
FIG. 23D is a sectional partial cut-away elevation view of the bone screw and insertion tool of FIG. 23A, showing the section 23D in FIG. 23C.
Figure 23E:
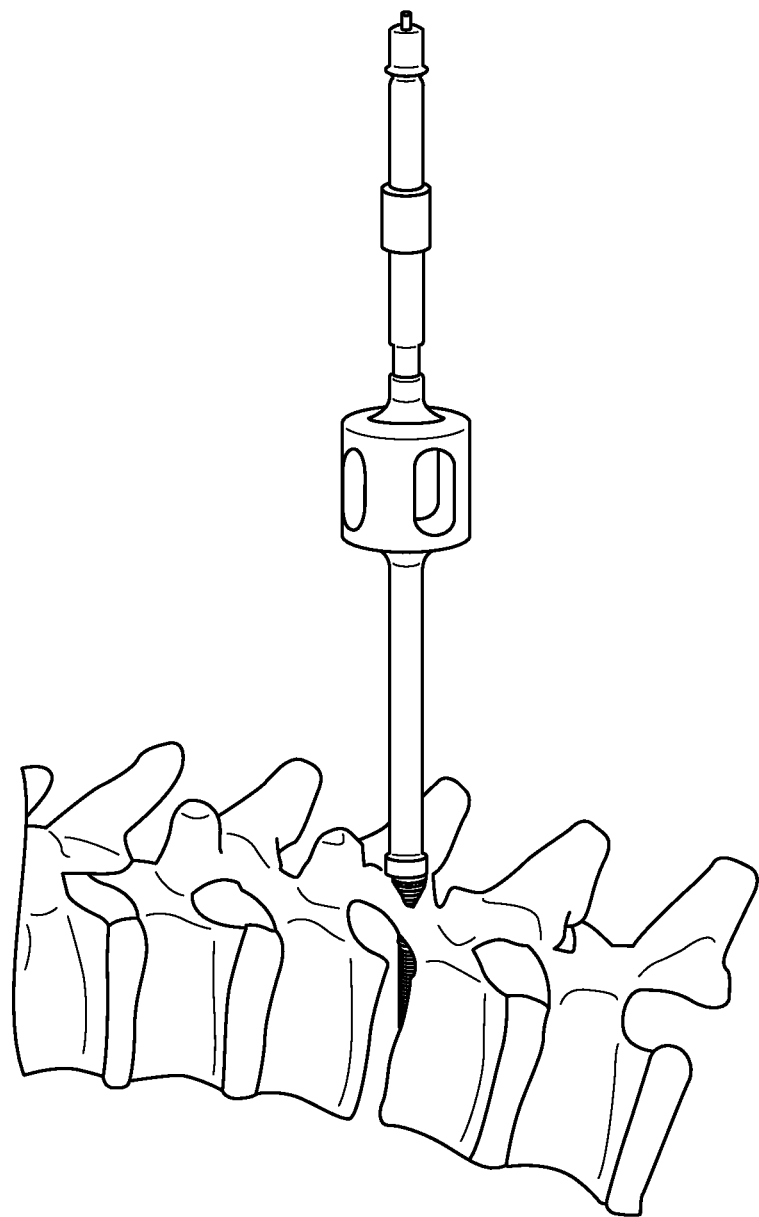
Figure 23G:
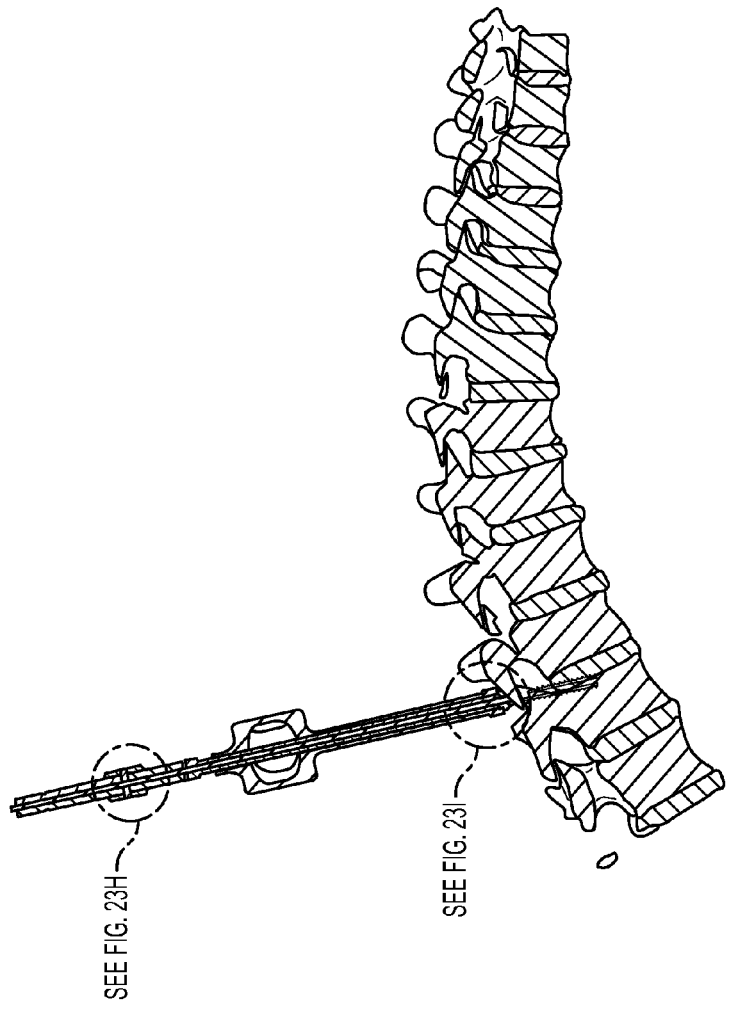
Figure 23F:
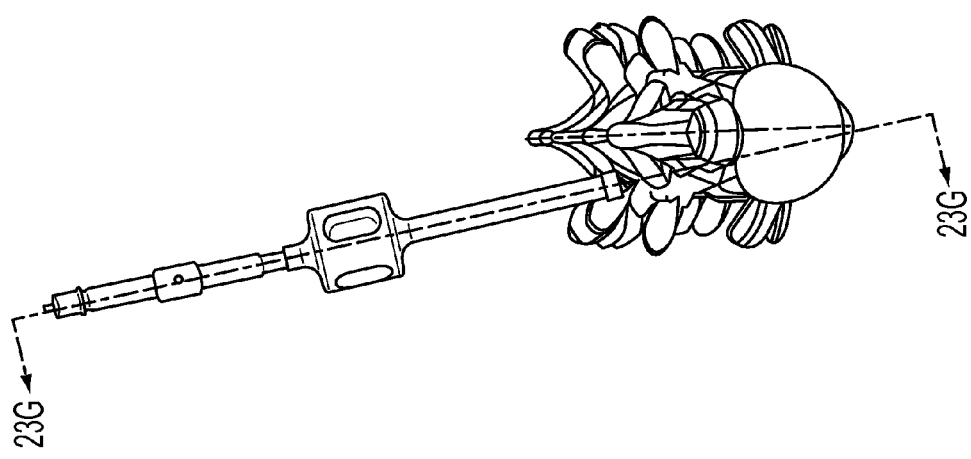
Figure 23I:
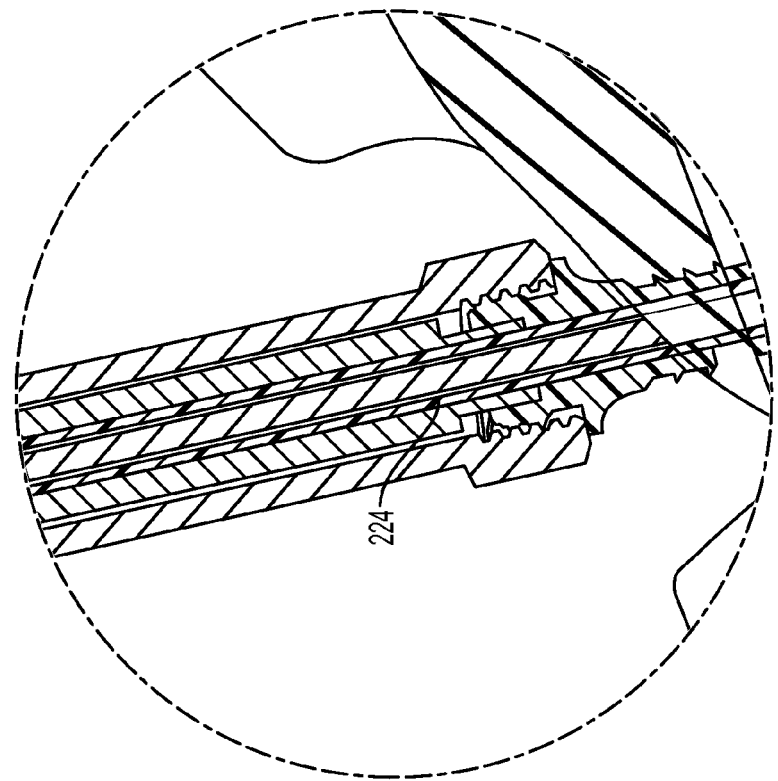
Figure 23H:
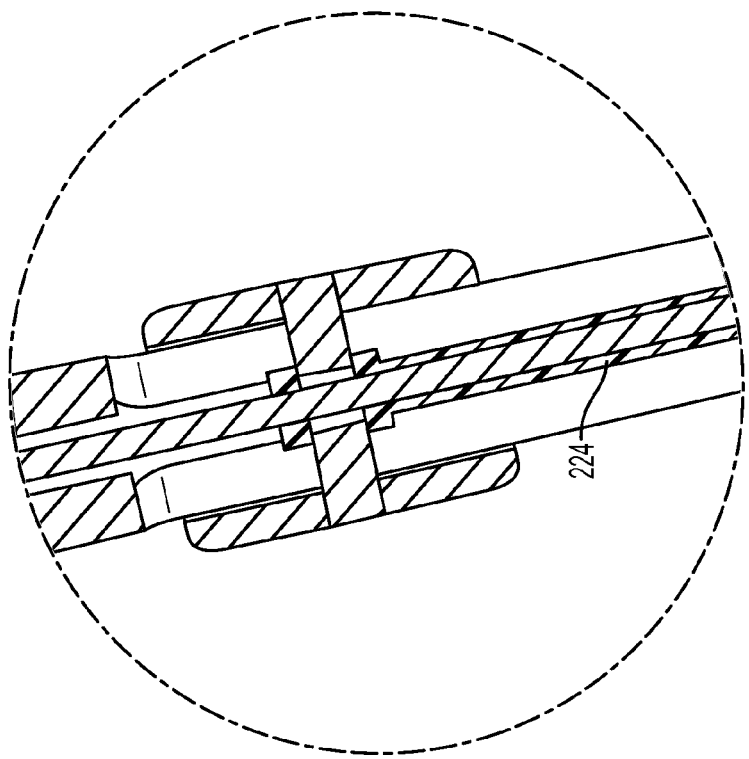

23E is a perspective view of one aspect of a bone screw and an insertion tool for inserting a bone screw;

FIG. 23F is a front elevational view of the bone screw and insertion tool of FIG. 23E;

FIG. 23G is a partial cut away side elevational view of the bone screw and insertion tool of FIG. 23F, cut along line 23G-23G of FIG. 23F;

FIG. 23H is a sectional partial cut-away elevation view of the bone screw and insertion tool of FIG. 23E, showing the section 23H in FIG. 23G; and FIG. 23I is a sectional partial cut-away elevation view of the bone screw and insertion tool of FIG. 23E, showing the section 23I in FIG. 23G.

DETAILED DESCRIPTION

The present systems and apparatuses and methods are understood more readily by reference to the following detailed description, examples, drawing, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an" and "the" include plural referents unless the context clearly dictates otherwise. Thus, for example, reference to "a" component can include two or more such components unless the context indicates otherwise. Also, the words "proximal" and "distal" are used to describe items or portions of items that are situated closer to and away from, respectively, a user or operator such as a surgeon. Thus, for example, the tip or free end of a device may be referred to as the distal end, whereas the generally opposing end or handle may be referred to as the proximal end.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

The term "substantially" as used herein may be applied to modify any quantitative representation which could permissibly vary without resulting in a change in the basic function to which it is related.

Figure 1:
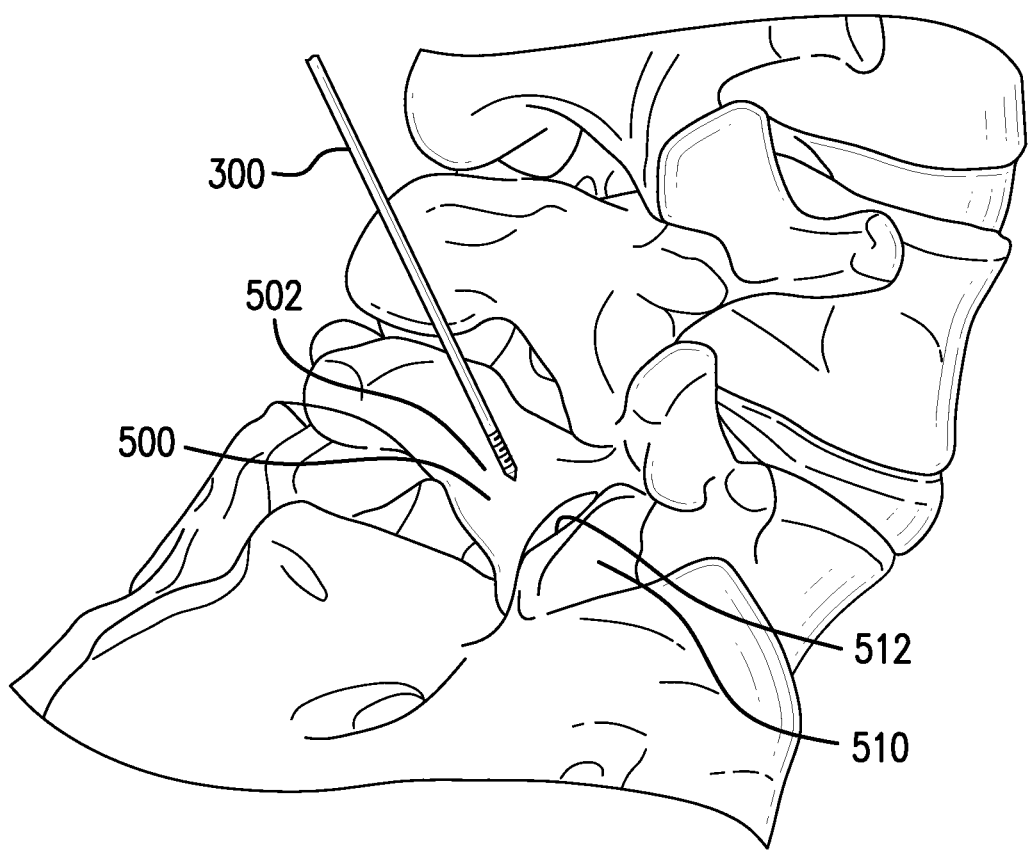
FIG. 1 is a perspective view of one aspect of a method for stabilization across a bone joint in the spine, showing the step of inserting a guide wire along a selected trajectory to cross a bone joint of the desired motion segment.

Presented herein are systems, tools, and methods for accessing the interior of a body and performing a medical procedure such as the stabilization of a motion segment of the human spine. A motion segment generally includes two adjacent vertebrae, the intervertebral disc, and the adjoining ligaments. For example, FIG. 1 illustrates a first vertebral bone 500 and a second vertebral bone 510. A stabilization procedure, for example, may include fastening or fixing a superior facet 502 of the first vertebral bone 500 to an inferior facet 512 of the second vertebral bone 510. In some embodiments, described herein, an apparatus can be inserted and secured to the adjacent bones, and a device may be used to inject bone fusion material to facilitate and improve stabilization of the motion segment. The bone fusion material may comprise, for example and without limitation, autologous bone, allograft bone, bone substitute, osteoinductive agent, and bone cement.

Presented herein is a system 10 for use in a bone stabilization procedure such as fixation and fusion. As described in more detail below, the system 10 may include a fenestrated bone screw and an insertion tool. The insertion tool may include a cannula and a drive rod. The insertion tool may be aided by a guide wire. The system may include a drill for preparing a hole for the screw. The system may also include a syringe for forcibly inserting bone fusion material.

Figure 8:
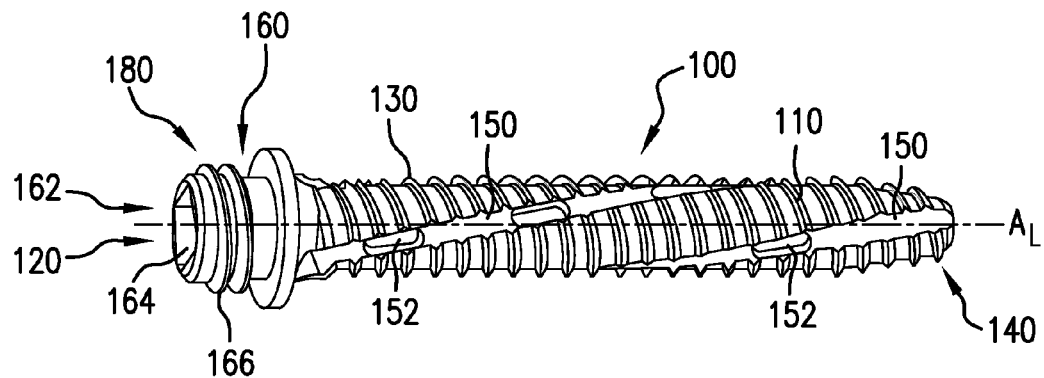
FIG. 8 is a perspective view of one aspect of a bone screw showing its external threaded surface that defines a substantially longitudinal groove and a shank aperture in communication with the internal longitudinal passage and the substantially longitudinal groove.
Figure 9:
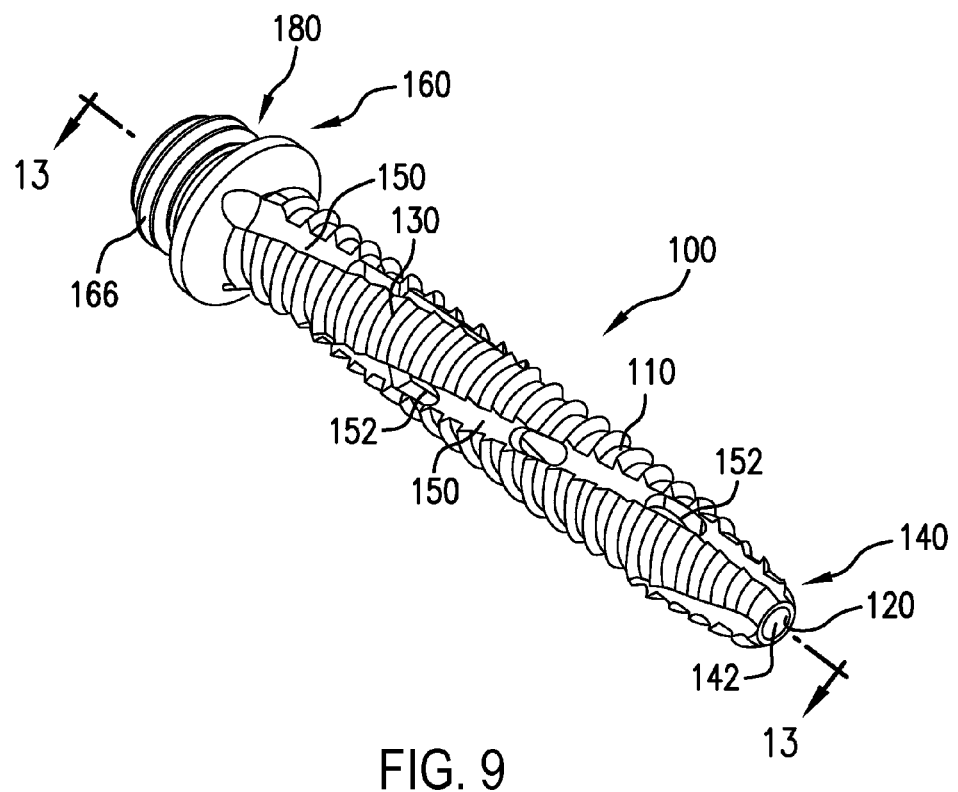
FIG. 9 is a perspective view of one aspect of the bone screw of FIG. 8.
Figure 10:
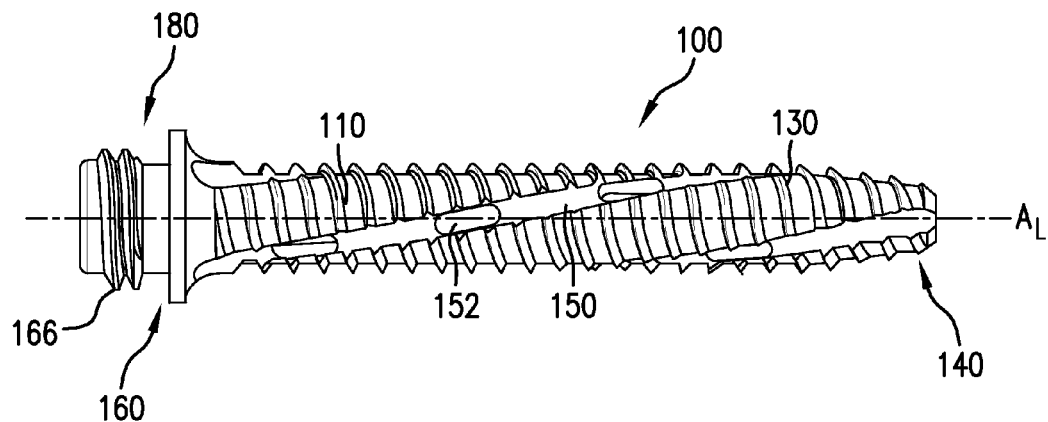
FIG. 10 is a side elevational view of one aspect of the bone screw of FIG. 8.
Figure 13:
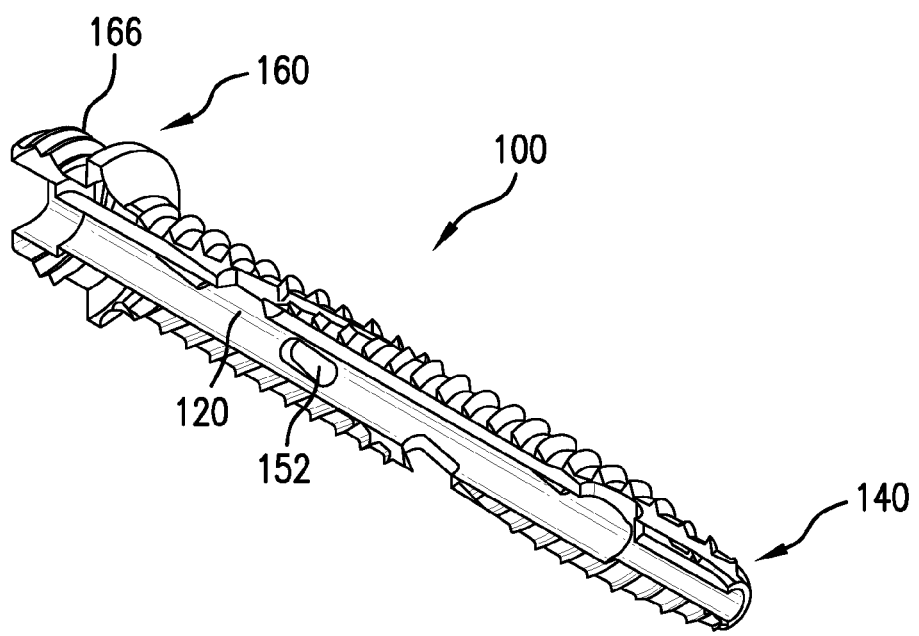
FIG. 13 is a cut-away perspective view of one aspect of the bone screw of FIG. 8, cut along line 13-13 of FIG. 9.

In one aspect, presented herein is a screw 100 for bone fixation. The bone screw 100, in an exemplified aspect, comprises a head portion 160 and an elongate shank 110 defining an internal longitudinal passage 120, as shown in FIG. 13. In one embodiment, the screw 100 may be a lag screw, wherein part of the shank near the head has no external thread. The shank has an external thread 130 and a tapered distal end 140, as shown in FIGS. 8-10. In one aspect, the external thread 130 defines at least one substantially longitudinal groove 150. In another aspect, the shank defines at least one shank aperture 152 that is connected to or otherwise in communication with the internal longitudinal passage 120. The shank aperture can be positioned therein the at least one substantially longitudinal groove. In this aspect, the shank aperture is in communication with the internal longitudinal passage and the substantially longitudinal groove 150.

Figure 12:
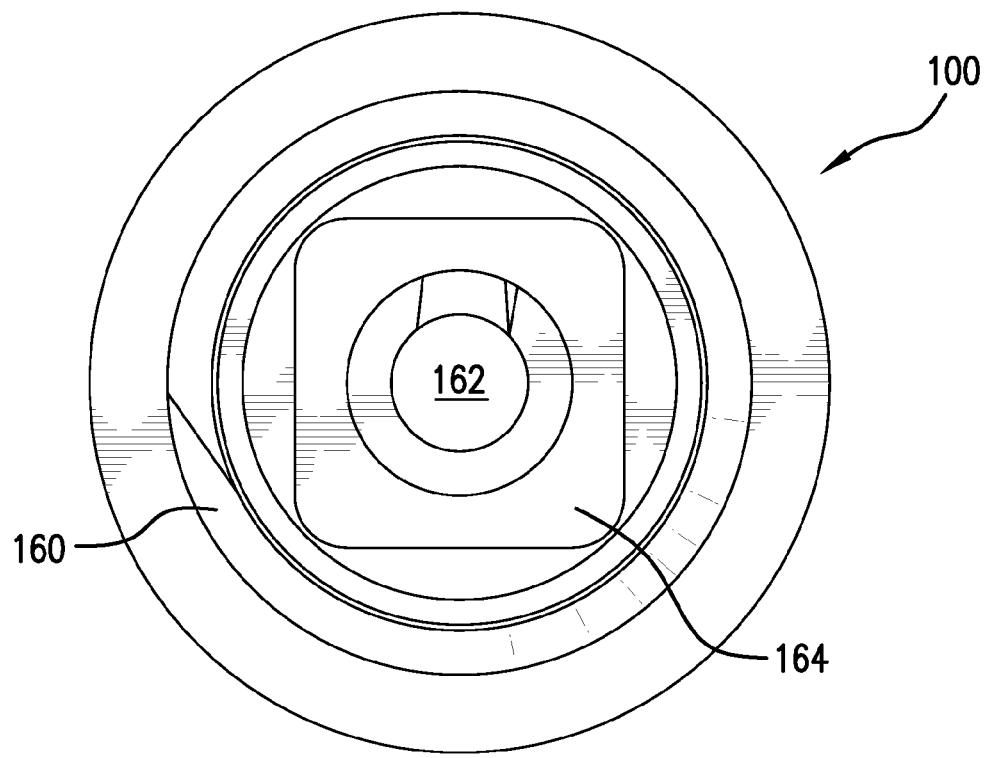
FIG. 12 is a proximal end elevation view of one aspect of the bone screw of FIG. 8.
Figure 15:
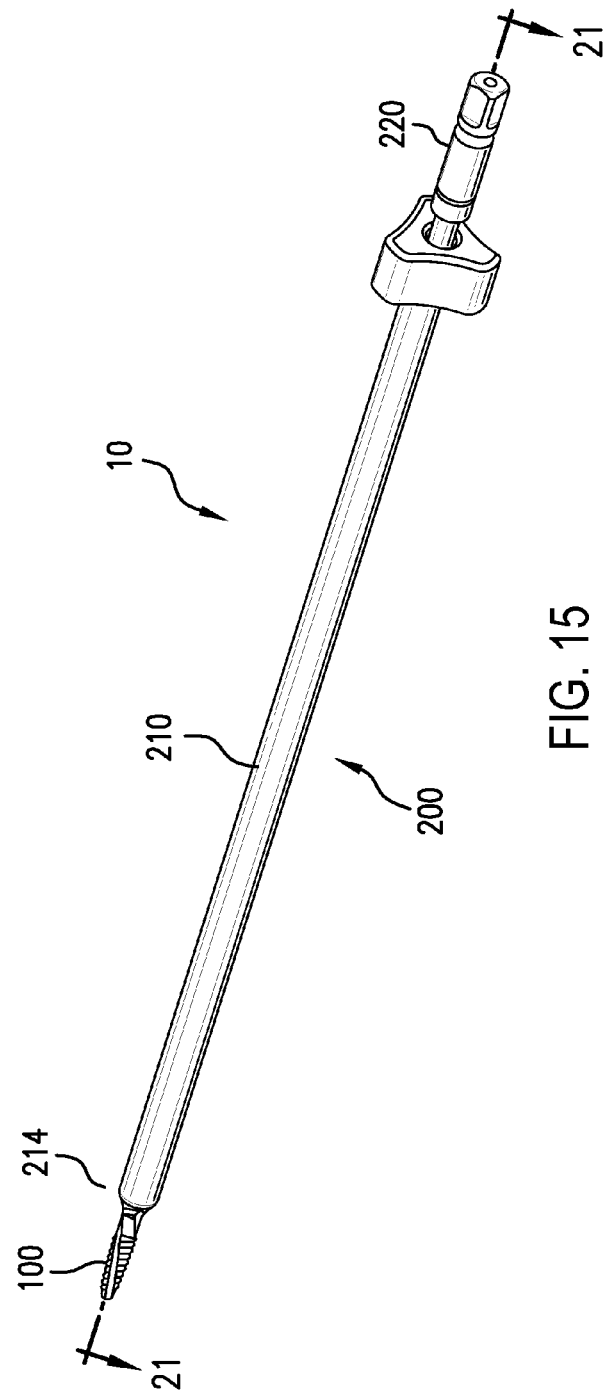
FIG. 15 is a perspective view of one aspect of the insertion tool of FIG. 14.

The head portion 160 of the screw may be positioned at the proximal end 180 of the shank 110. The head portion 160 may be configured for engagement with an insertion tool 200 (shown in FIG. 15 and discussed below). In another aspect, the head portion 160 of the screw defines a head aperture 162 that is connected to or otherwise in communication with the internal longitudinal passage 120, as shown in FIG. 12. The head aperture 162 provides a path whereby fluid (such as bone fusion material) can flow through the head aperture 162, into and through the internal longitudinal passage 120, through the at least one shank aperture 152, and into the surrounding area where the screw 100 is positioned.

The substantially longitudinal groove 150 may comprise one groove, or a plurality of grooves that are spaced apart from one another, as shown in FIG. 9. The grooves 150 may be positioned such that they are substantially parallel to the longitudinal axis $A_L$ of the elongate shank, but are not necessarily so. In another aspect, the grooves are positioned at an acute angle relative to a longitudinal axis of the shank.

Additionally, there can be more than one shank aperture 152, and when the shank aperture is positioned therein a groove, there may be more than one shank aperture in each groove 150, depending upon the geometry of the groove. As one skilled in the art can appreciate, if too many shank apertures 152 are positioned in each groove 150, less material would be present in the structure, potentially weakening the shank 110. The shank aperture 152 can have any of a variety of shapes. In one embodiment, the shank aperture 152 may be elongated in a direction that is substantially parallel to the groove 150, as illustrated in FIG. 9.

Figure 11:
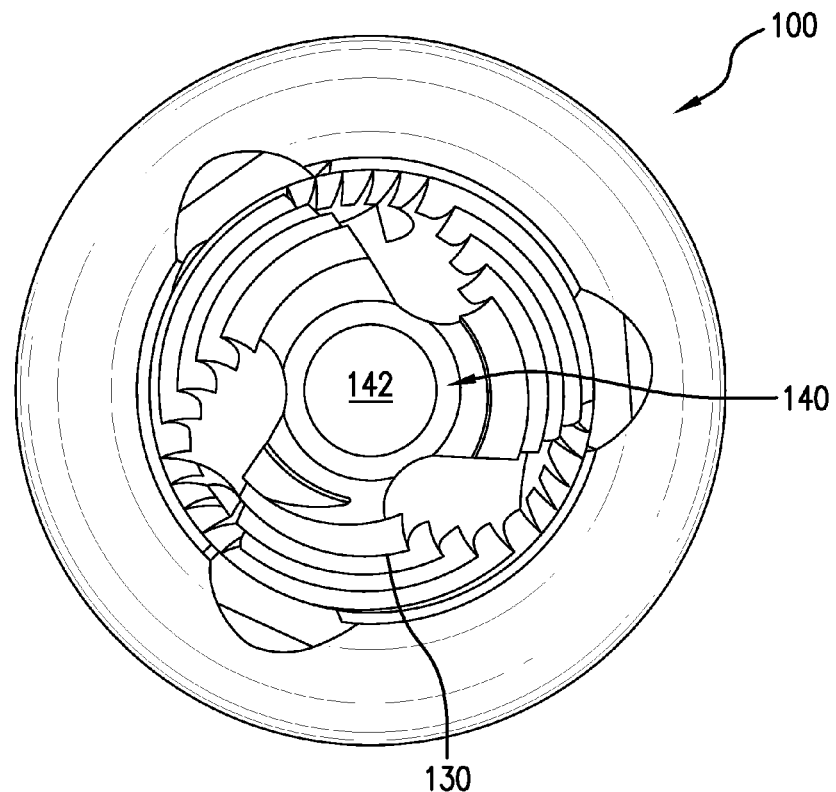
FIG. 11 is a distal end elevational view of one aspect of the bone screw of FIG. 8.

In another embodiment, the distal end 140 of the elongate shank defines a tip aperture 142 (shown in FIG. 11) that is connected to or otherwise in communication with the internal longitudinal passage 120. Together with the head aperture 162 and the internal passage 120, the tip aperture 142 provides a complete passageway through the screw 100 from the proximal end 180 to the distal end 140, as shown in FIG. 13. In this aspect, the tip aperture 142 is part of a pathway whereby fluid (such as bone fusion material) can flow through the head aperture 162, through the internal longitudinal passage 120, through the shank apertures 152, through the tip aperture 142, and into the surrounding area where the screw 100 is positioned. These apertures 142, 152, 162, together or separately, may be referred to as fenestrations in the bone screw 100 and may be designed in size and shape and arranged geometrically along the screw in any of a variety of ways that best facilitates a particular use or application.

As illustrated in FIG. 12, in one exemplified aspect, the head portion 160 may include a keyed portion such as a head cavity 164 that is sized and shaped for complimentary receipt of a portion of an insertion tool 200 (discussed below). The portion head 160 may also comprise an external head thread 166 that is configured to mate with a corresponding internal thread on a portion of an insertion tool 200.

Figure 14:
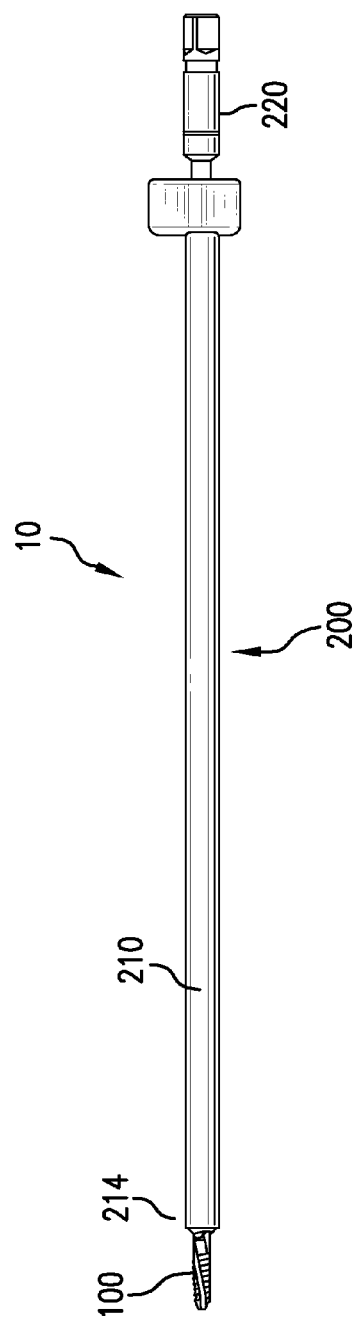
FIG. 14 is a side elevational view of one aspect of an insertion tool for inserting a bone screw.
Figure 16:
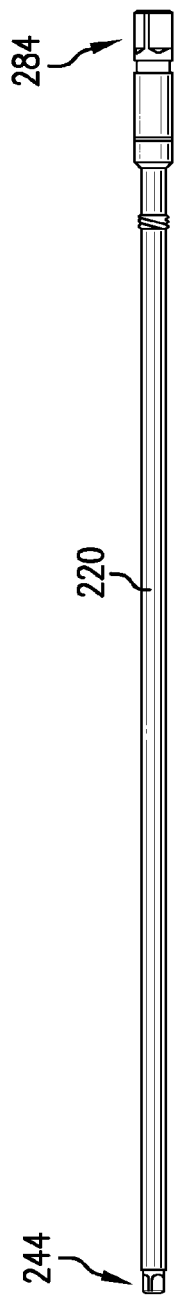
FIG. 16 is a side elevational view of one aspect of a drive rod for the insertion tool of FIG. 14.
Figure 17:
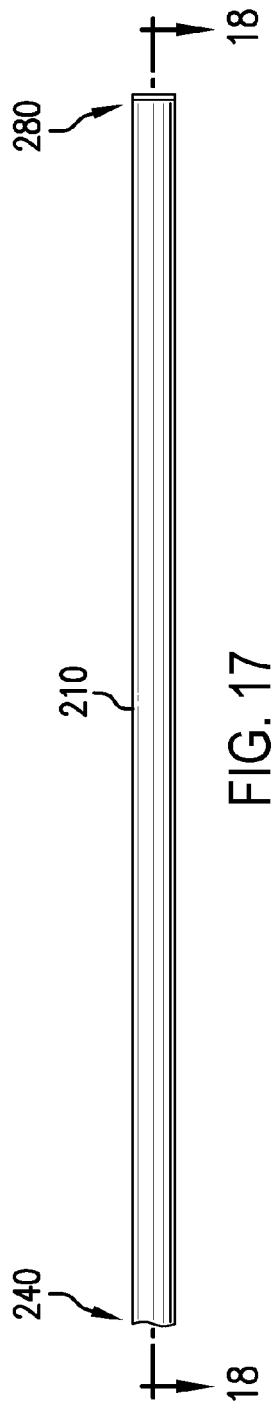
FIG. 17 is a side elevational view of one aspect of an elongate tube for the insertion tool of FIG. 14.

In one embodiment, an insertion tool 200 is provided for use with a bone screw 100 such as the fenestrated bone screw 100 described above. The insertion tool 200 may include a drive rod 220 and an elongate hollow tube or cannula 210, as shown in FIG. 14. The cannula 210 has a proximal end 280 and a distal end 240, as shown in FIG. 17. The drive rod 220 has a proximal end 284 and a distal end 244, as shown in FIG. 16. In use, the drive rod 220 may be inserted into the lumen 264 of the cannula 210, as shown in FIG. 21. The drive rod 220 is selectively removable from the lumen 264 of the cannula 210.

As illustrated in FIG. 16, the proximal end 284 of the drive rod 220 may include a handle. The distal end 244 may be configured to mate with and drive a bone screw 100. As described above, a portion of the head 160 may be keyed for complimentary receipt of the distal end 244 of the drive rod. In this aspect, the distal end 244 can be configured to be received into a head cavity 164 that has been complimentarily keyed.

The drive rod 220 may have an internal longitudinal passageway or lumen 224, as shown in FIGS. 21 and 22. In certain embodiments, the lumen 224 extends along the entire length of the drive rod 220 from the proximal end 284 to the distal end 244, where it may be sized and shaped to align with the head aperture 162 of the bone screw 100, as shown in FIG. 22. In this aspect, the distal end 244 of the drive rod 220 provides a closed channel from the lumen 224 into the internal longitudinal passage 120 of the screw 100.

Figure 18:
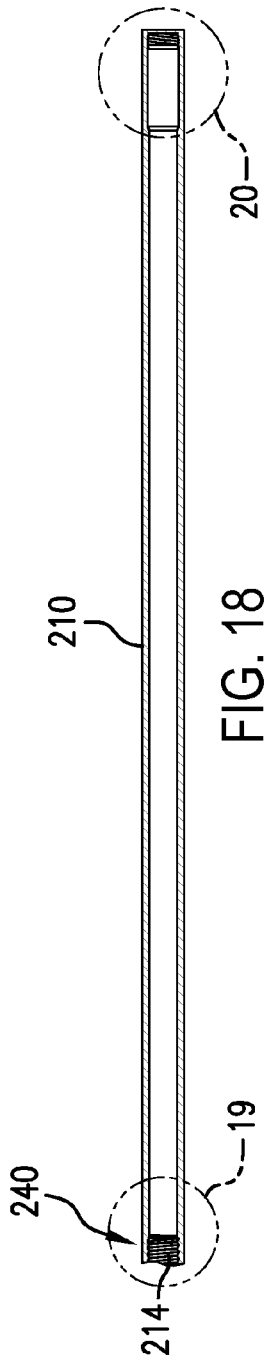
FIG. 18 is a cut-away side elevational view of one aspect of the elongate tube of FIG. 17, cut along line 17-17.

The distal end 240 of the cannula 210 may be configured to mate with the head portion 160 of the screw 100. For example, as illustrated in FIGS. 18 and 19, the distal end 240 of the cannula 210 may include an internal thread 214. The internal thread 214 may be configured to engage with the external head thread 166 of the bone screw 100, as shown in FIG. 22.

The proximal end 280 of the cannula 210 may include an entry cavity 250 and an internal entry thread 254, as illustrated in FIGS. 18 and 20. The entry cavity 250 may be somewhat larger in diameter than the lumen 264 of the cannula 210, and there may be a tapered region, as shown in FIG. 20, between the entry cavity 250 and the lumen 264. The internal entry thread 254 may be configured to engage with the complimentary thread of a tool, such as a stylet or a syringe 700 (described below).

Figure 2:
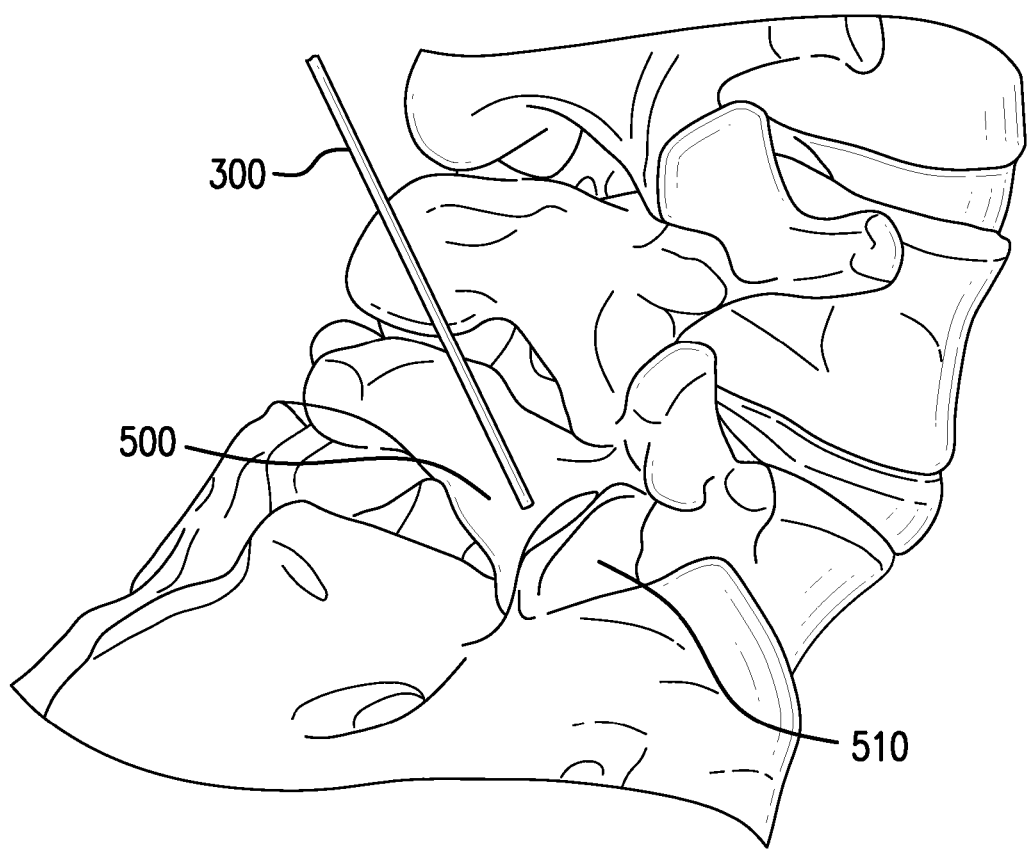
FIG. 2 is a perspective view of one aspect of the method of FIG. 1, showing the guide wire in place.
Figure 3:
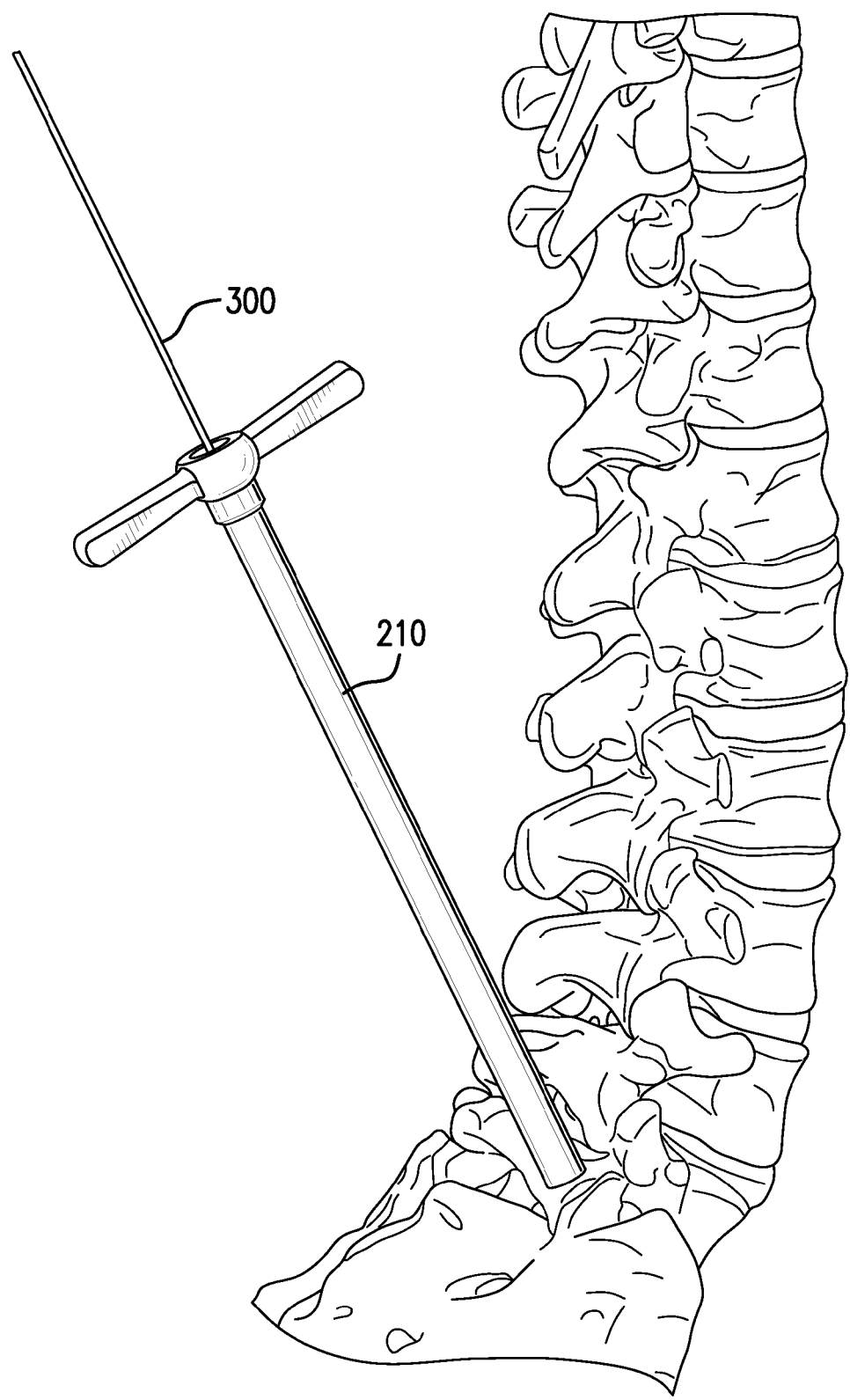
FIG. 3 is a perspective view of one aspect of the method of FIG. 1, showing the step of placing an access portal over the guide wire.
Figure 5A:
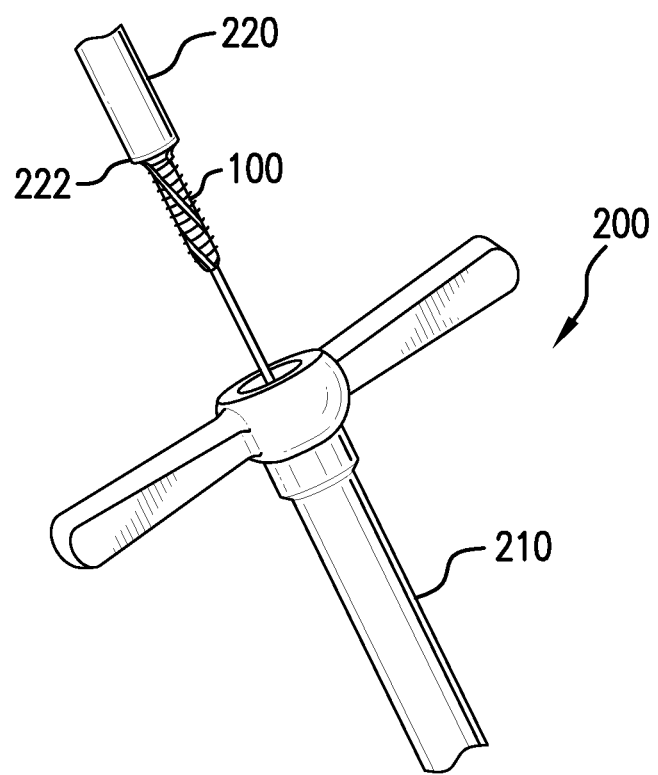
FIGS. 5A-5D are perspective views of one aspect of the method of FIG. 1, showing the step of placing a screw over the guide wire and driving it across a bone joint.

In another embodiment, the lumen 224 of the drive rod 220 may be sized for complimentary receipt of a guide wire 300. The guide wire 300 may be a smooth steel pin such as a Kirschner wire with a threaded distal tip to provide an anchor, as shown in FIGS. 1 and 2 and described below. Likewise, the internal longitudinal passage 120 of the screw 100 may be sized for complimentary receipt of a guide wire 300, as illustrated in FIG. 5A.

In another aspect, as shown in Detail E of FIG. 23, the lumen can be configured to extend into the internal passage substantially the entire length of the screw 100. In this aspect, the lumen acts to close the internal passage when the bone screw is driven into position. This prevents bone, fluid, and other debris from entering the internal passage. Once the bone screw is positioned, the lumen can be packed with bone fusion material and the lumen can be removed, leaving the bone fusion material in the internal passage.

Also presented herein is a method for stabilization across a bone joint in the spine. The bone joint may, for example, be a facet joint and can be in the lumbar region of the spine, as illustrated in FIG. 1. The method comprises providing a bone screw 100, accessing a desired motion segment of the spine, driving the bone screw across the desired bone joint, and injecting bone fusion material into the proximity of the bone joint.

In one embodiment, the bone screw 100 is the fenestrated bone screw described herein, having an internal longitudinal passage therethrough the shank.

In one exemplified aspect, the method comprises the step of identifying and accessing a selected surgical site, such as a selected motion segment of the spine.

Next, a guide wire 300 may be inserted into the body, along a selected trajectory, to the selected motion segment. The guide wire 300 may include a threaded tip that can be forcibly driven or screwed into the bone and provide an anchor at the surgical site, as illustrated in FIGS. 1 and 2.

Figure 4A:
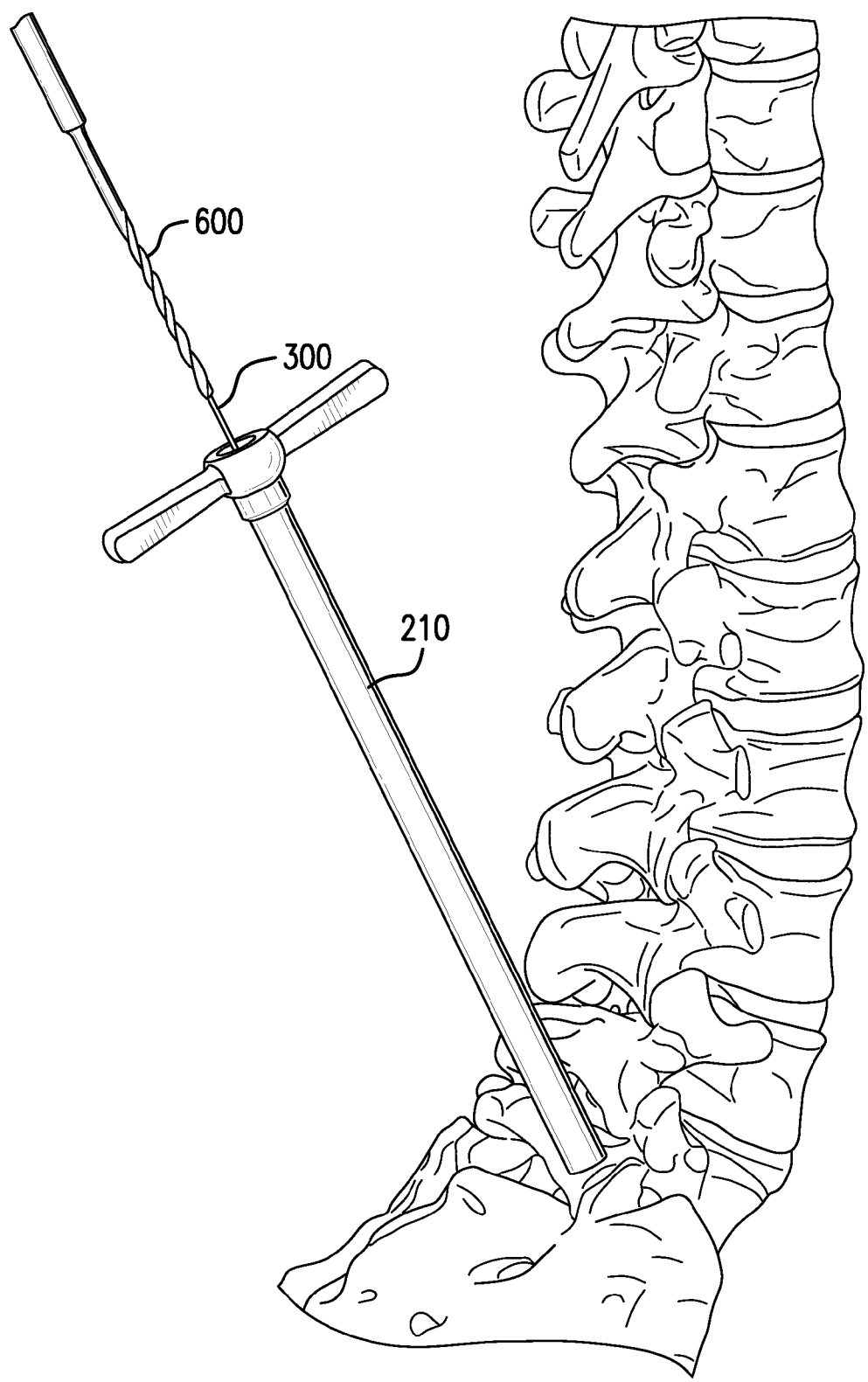
FIGS. 4A-4C are perspective views of one aspect of the method of FIG. 1, showing the step of passing a drill over the guide wire and pre-drilling a desired area of the bone joint.
Figure 4B:
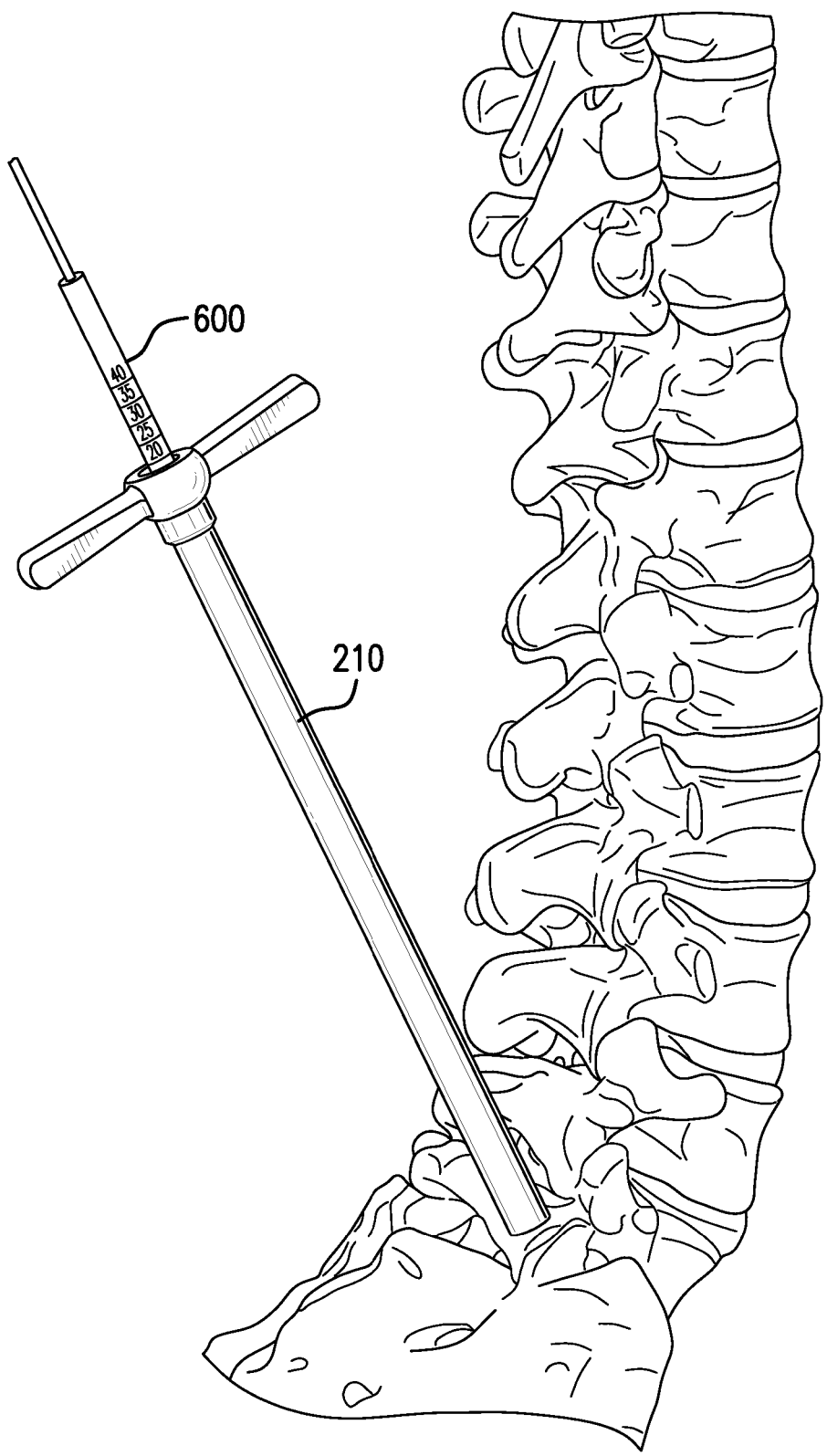
Figure 4C:
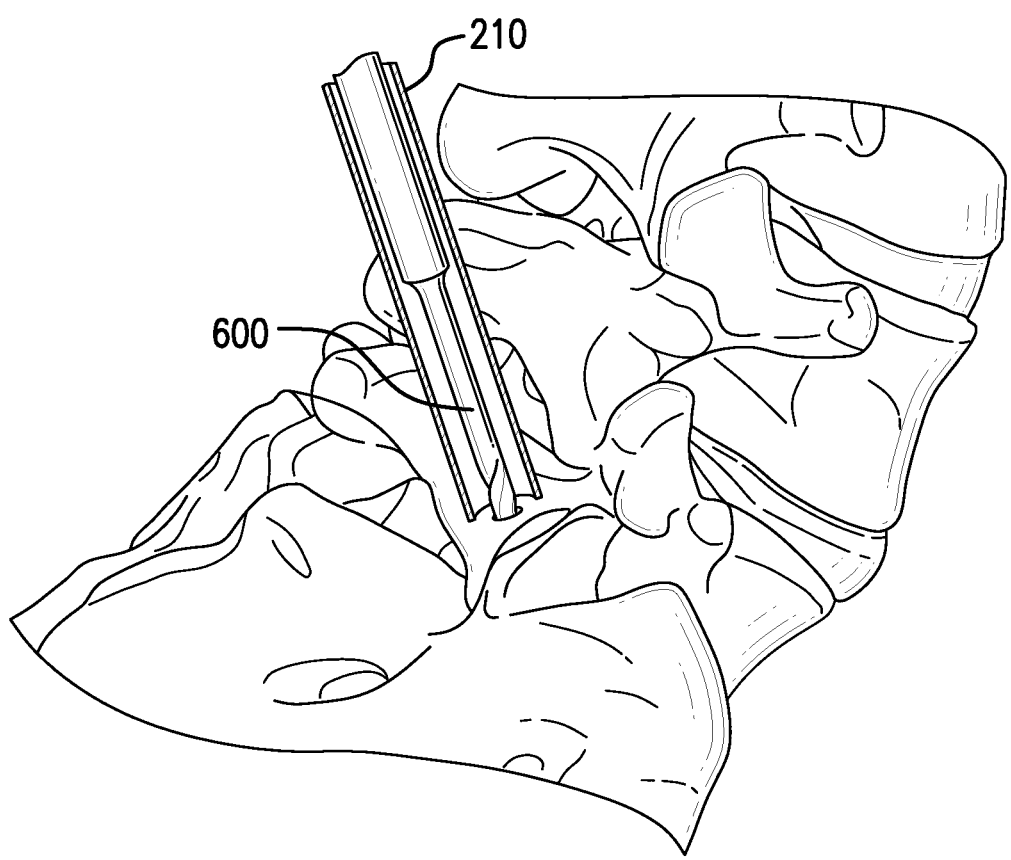

Next, in one embodiment, the lumen 264 of a cannula 210 may be placed over the guide wire 300, which guides the cannula 210 to the site. In embodiments where the system 10 includes a drill 600, as shown in FIG. 4A, the lumen of a drill 600 may be placed over the guide wire 300, which guides the drill bit to the surgical site. As shown in FIG. 4B, the drill 600 may include visible indicia related to the depth of the drill within the cannula 210 and, in some embodiments, the depth of the pilot hole in the bone at the surgical site. FIG. 4C illustrates the drill 600 inside the cannula 210 drilling a pilot hole into the bone.

Next, as illustrated in FIG. 5A, a bone screw 100 with an internal passage 120 may be placed over the guide wire 300. A cannula 210 may also be placed over the guide wire 300, with its distal end 240 resting against or otherwise engaged with the head portion 160 of the screw 100. As described above, the distal end 240 of the cannula 210 may include an internal thread 214 sized to engage with an external head thread 166 on the head of the screw 100. As shown, the cannula 210 may include a handle. Together, the bone screw 100 and cannula 210 are guided to the surgical site along the guide wire 300.

Figure 5B:
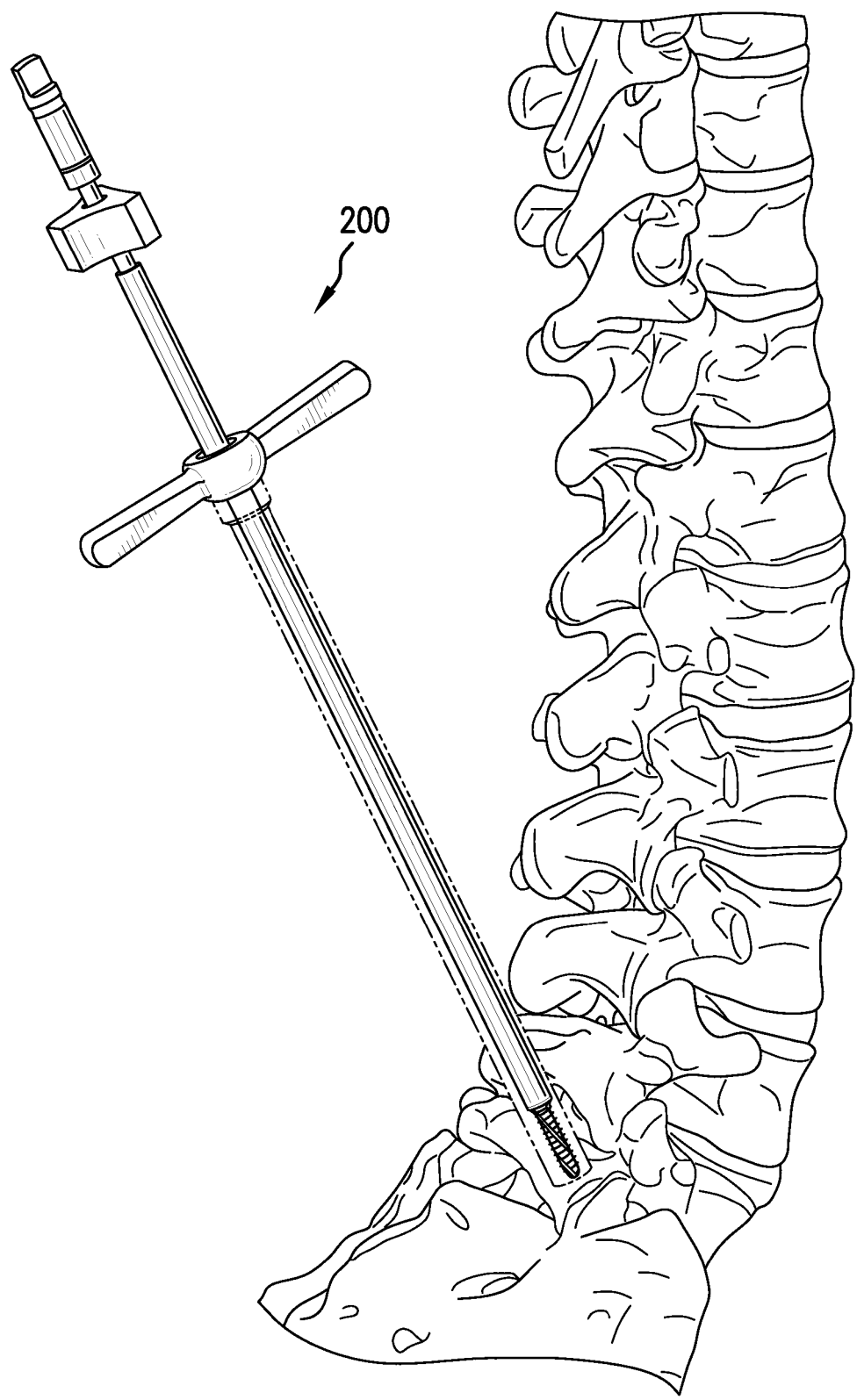
Figure 5C:
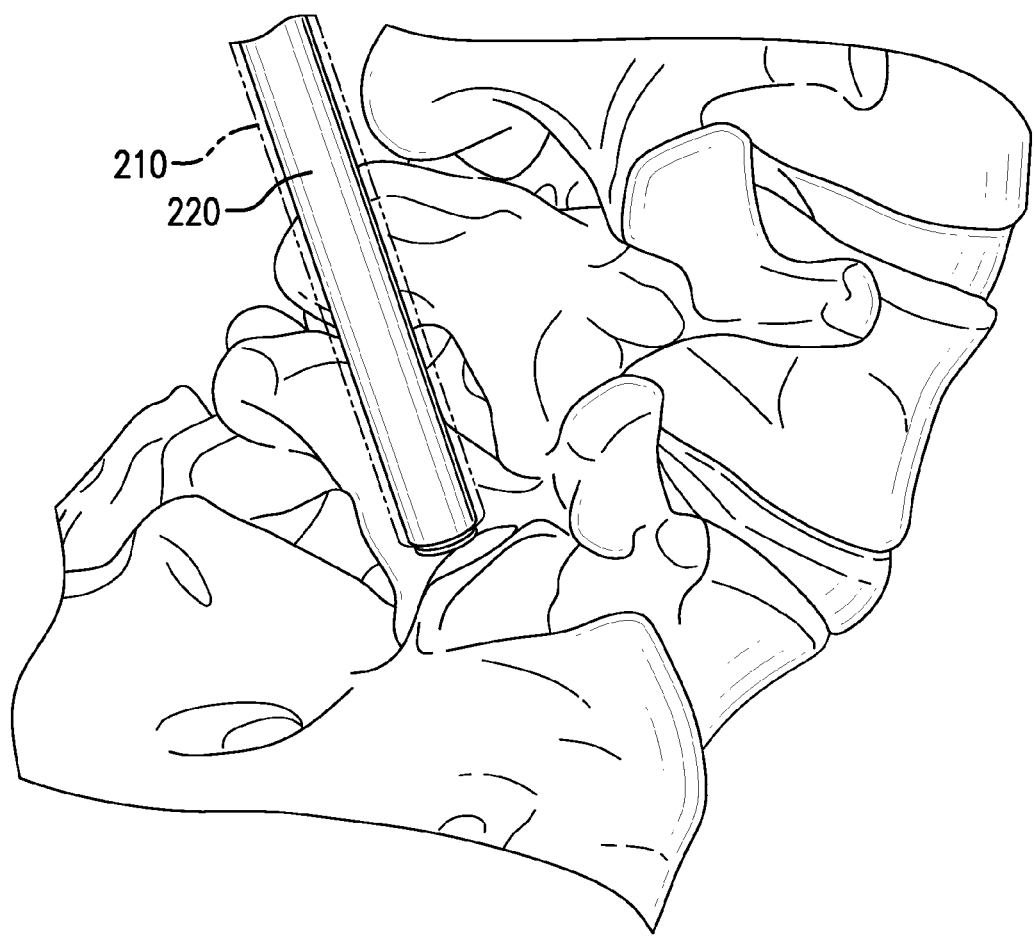
Figure 5D:
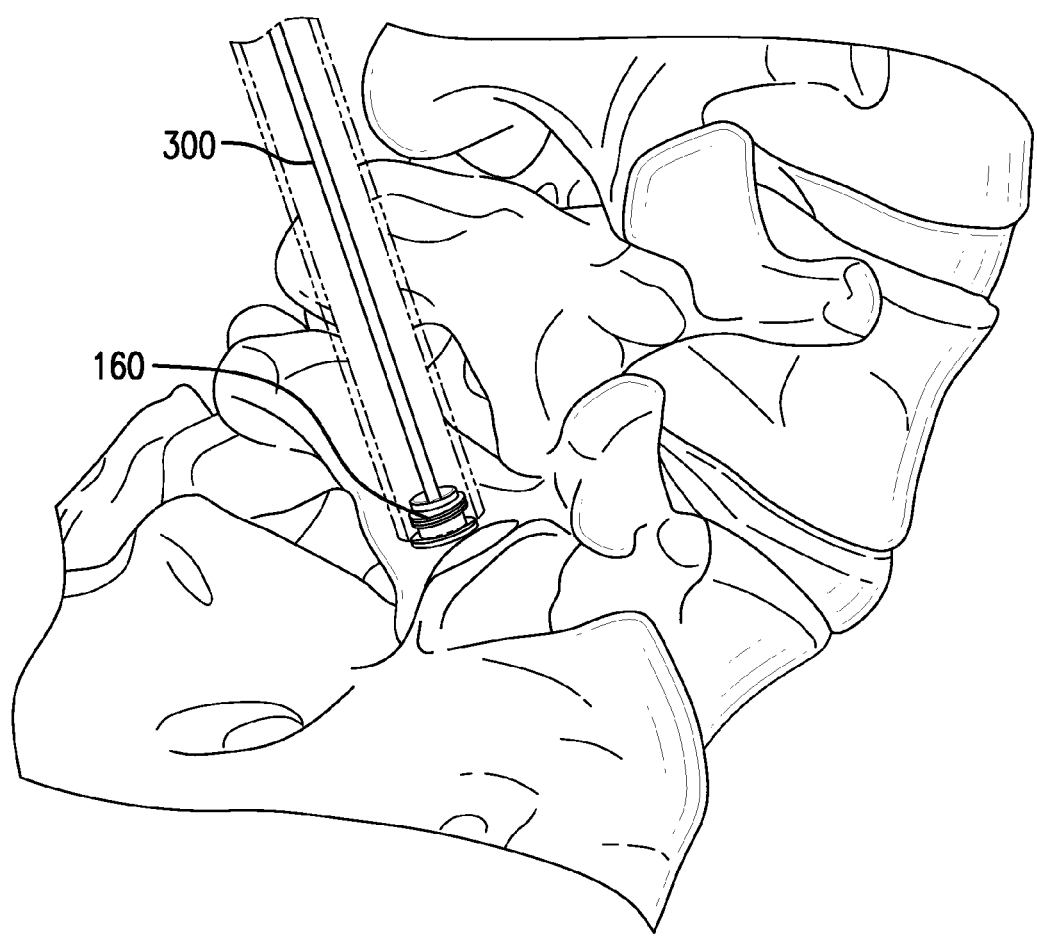
Figure 6A:
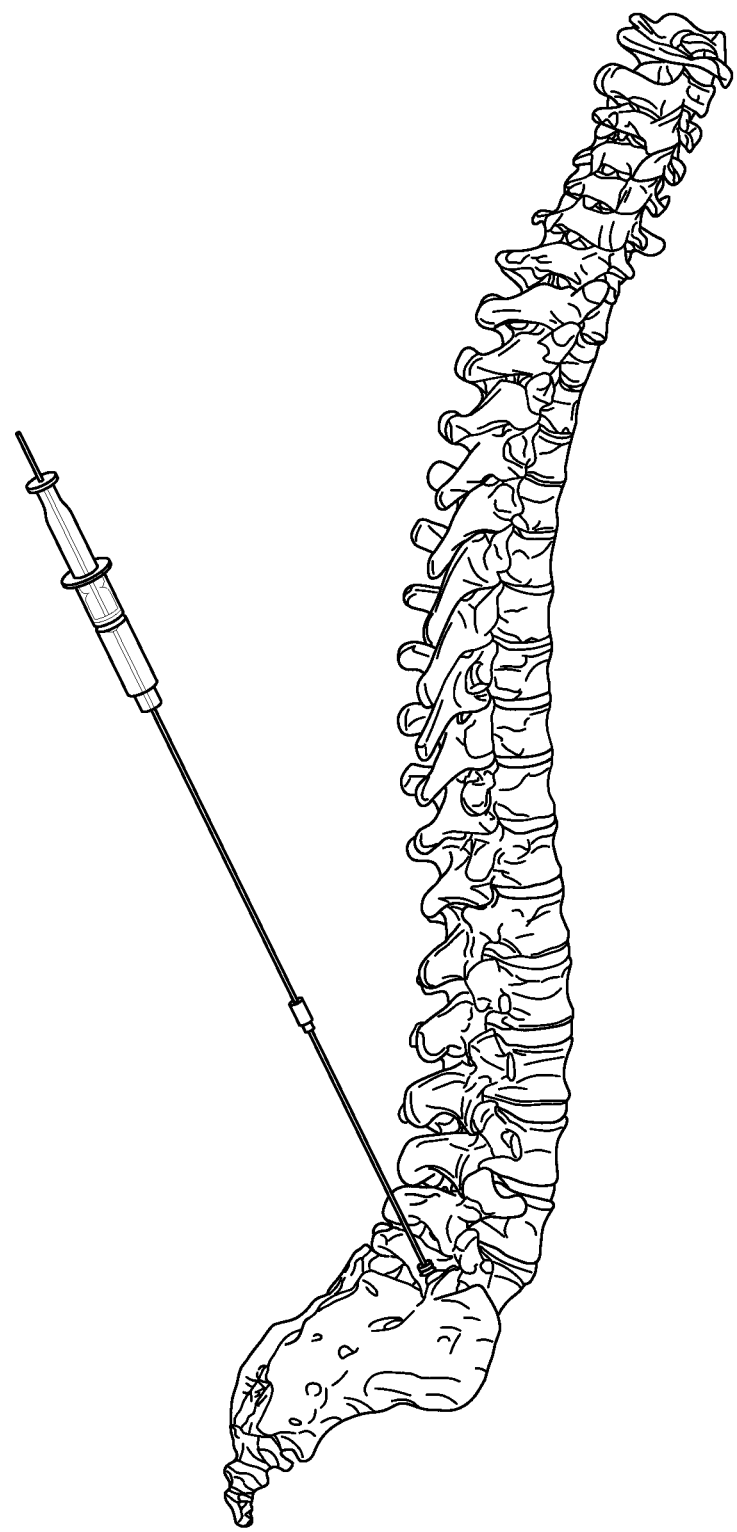
FIGS. 6A-6D are perspective views of one aspect of the method of FIG. 1, showing the step of injecting a radio-opaque substance into the internal passageway such that it secretes from the at least one shank aperture.
Figure 6B:
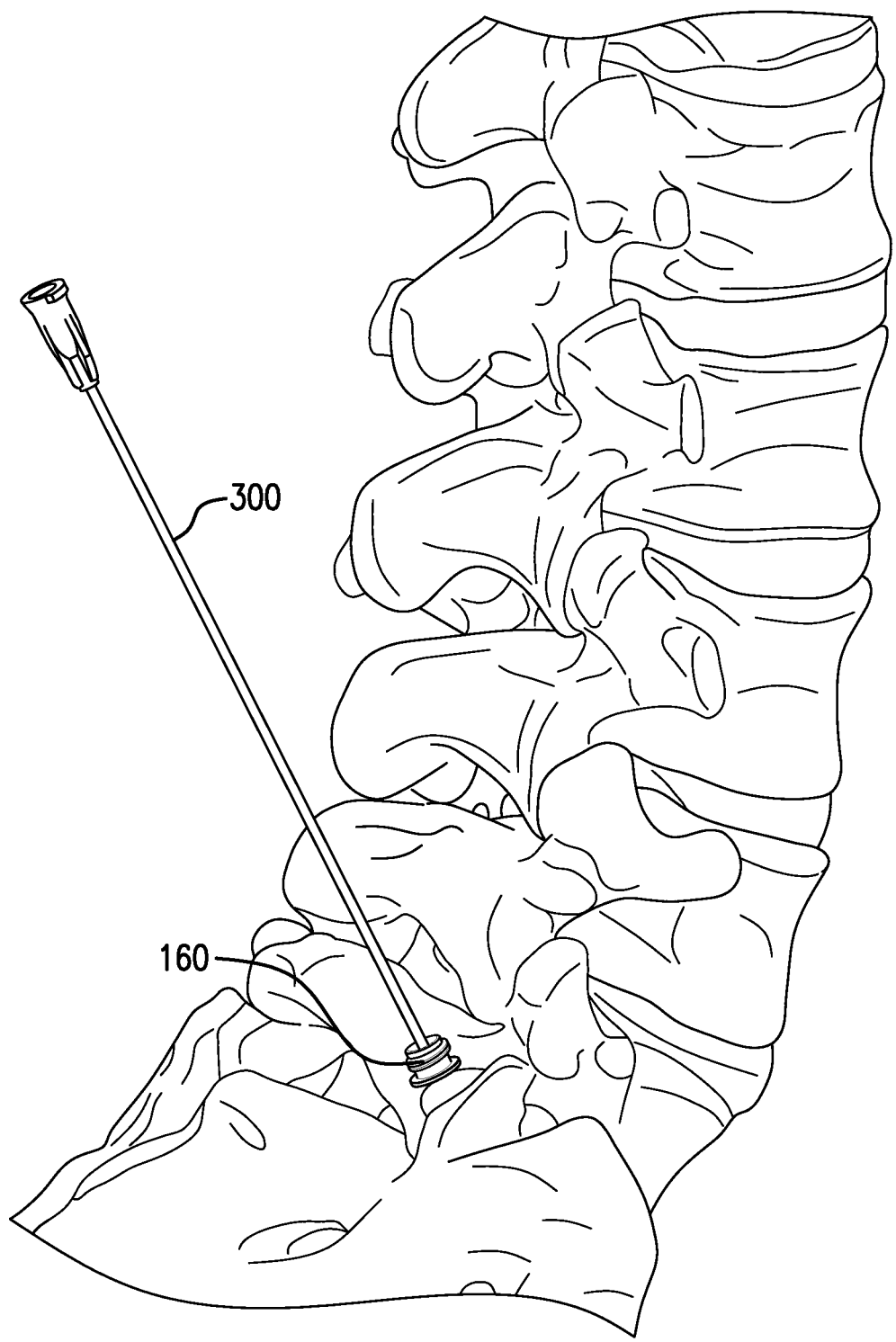
Figure 6C:
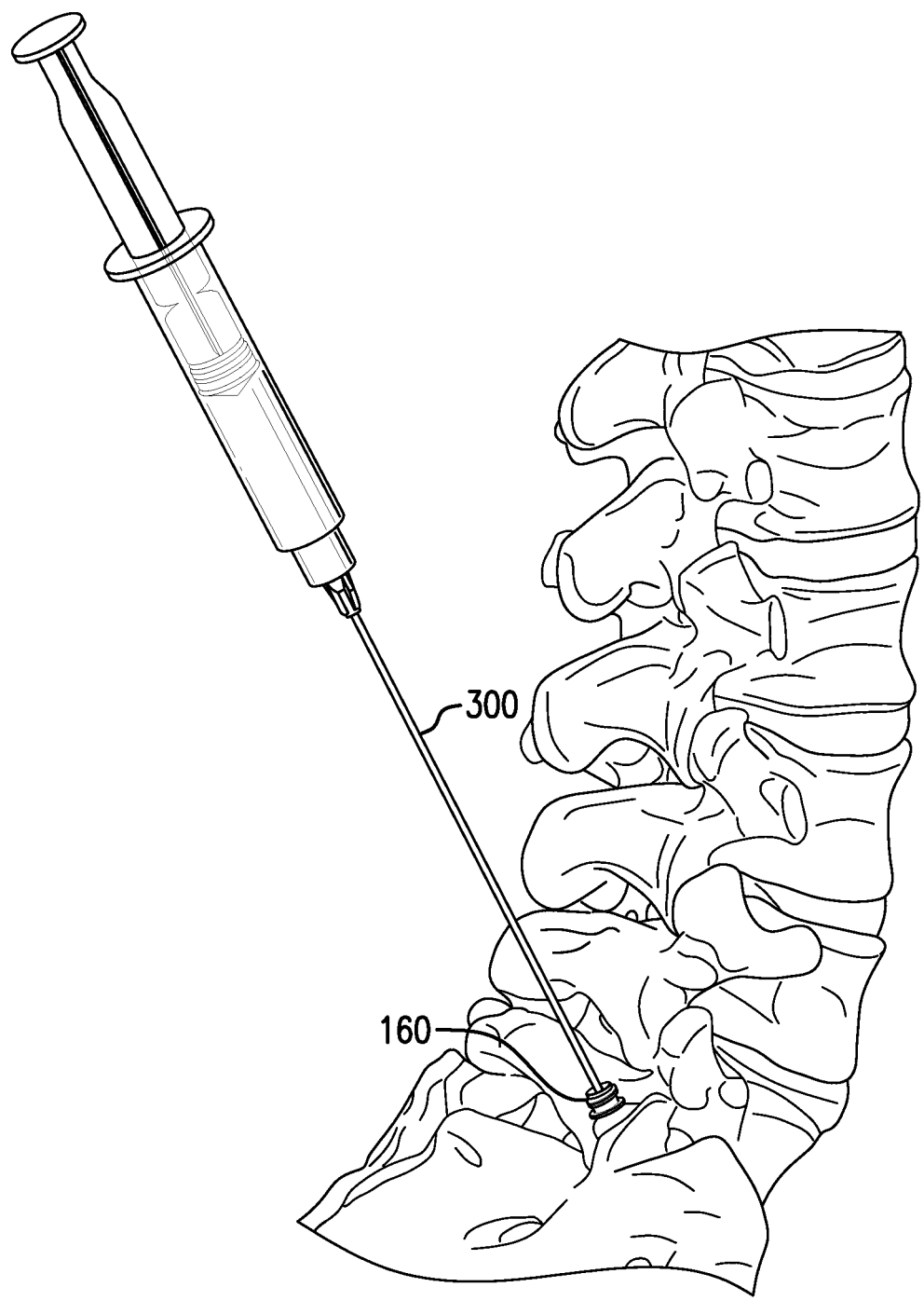
Figure 6D:
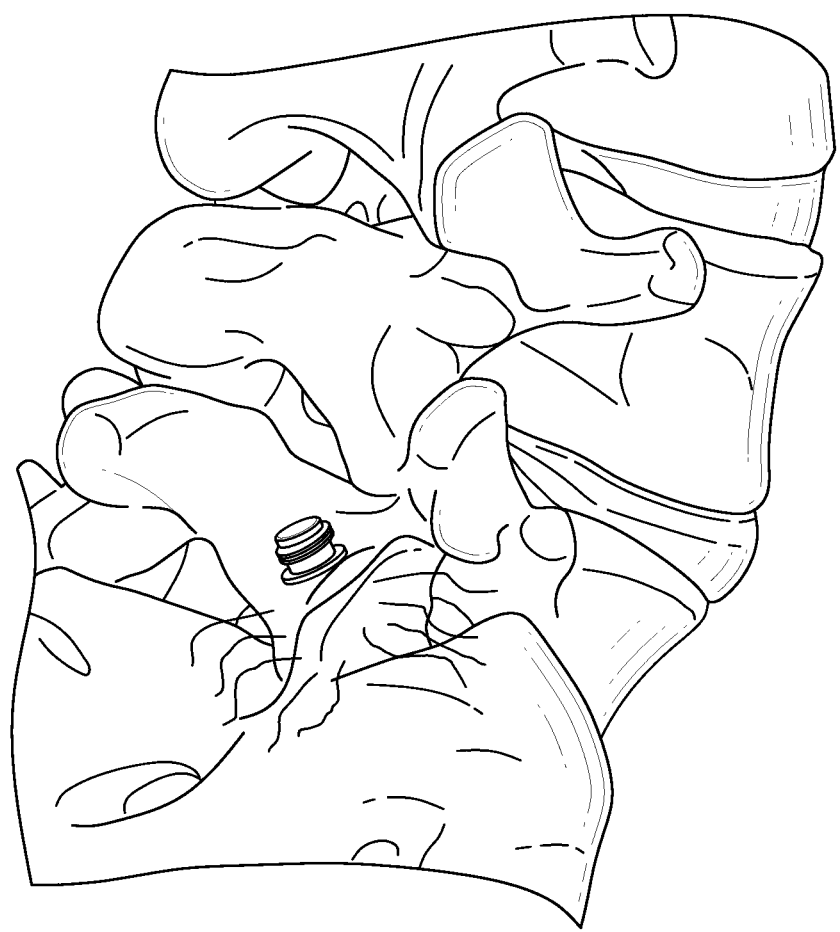
Figure 7A:
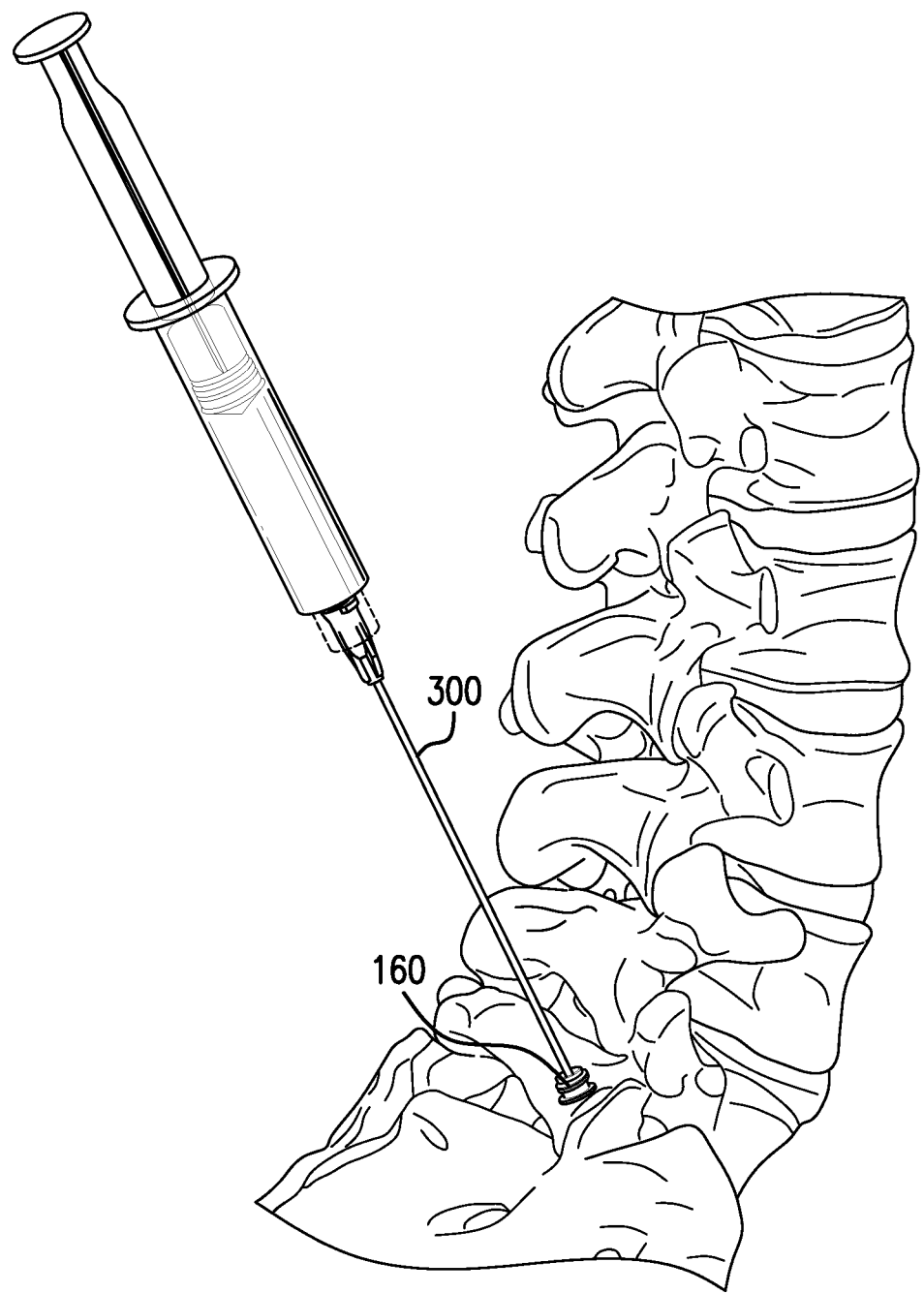
FIGS. 7A-7B are perspective views of one aspect of the method of FIG. 1, showing the steps injecting bone fusion material into the internal passageway such that it secretes from the at least one shank aperture and is placed in proximity to the bone joint in the lumbar region of the spine, wherein the bone fusion material is placed in proximity to the bone of a superior facet of a first vertebral bone and the inferior facet of a second adjacent vertebral bone
Figure 7B:
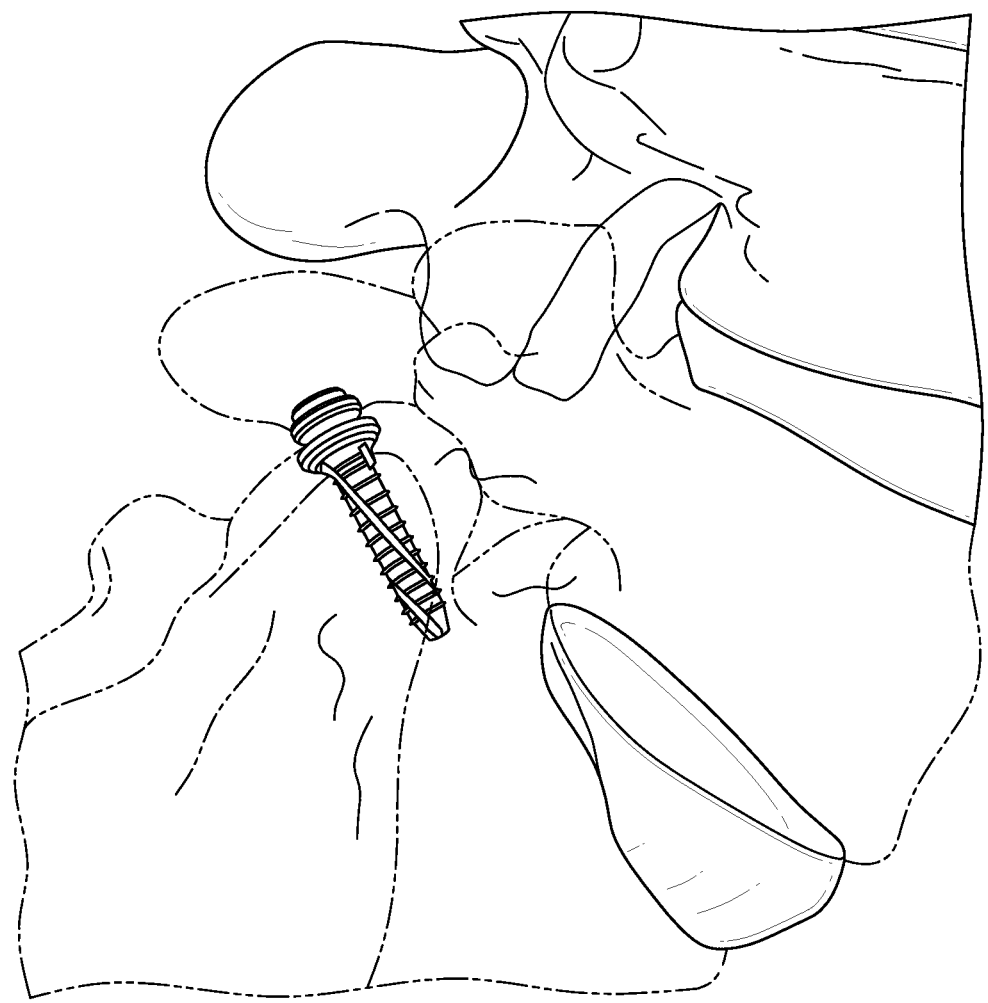

FIG. 5B illustrates the bone screw 100 at the surgical site, the cannula 210 (shown in dotted lines) surrounding the screw, and a drive rod 220 being inserted into the cannula 210. In this embodiment, the distal end of the drive rod may engage the head portion 160 and drive the screw 100 into the bone at the surgical site.

At this point, the guide wire 300 may be removed, leaving the lumens and the internal passage 120 of the screw 100 empty. In one embodiment, the method next includes the step of inserting bone fusion material 400 into the internal passage 120 of the screw 100, through the fenestrations such as the shank apertures 152, into the elongate grooves 150, and into the space surrounding the surgical site. This step can be accomplished, for example, by removing the drive rod 220, placing the bone fusion material into the cannula 210, and using a plunger or syringe 700 to forcibly push the bone fusion material into the fenestrated bone screw 100. In this aspect, the bone fusion material is injected into the internal longitudinal passage 120 such that it emerges through or secretes from the shank apertures 152 and is deposited in proximity to the bone joint. Due to the geometry of the elongate grooves 150, the secretion of the bone fusion material can travel along the groove 150, thus providing a greater surface area of contact between the screw and the surrounding bone. As can be appreciated, the bone fusion material can placed along and around the proximity of a bone screw 100 that spans the distance between a superior facet 502 of a first vertebral bone 500 and the inferior facet 512 of a second adjacent vertebral bone 510, as illustrated in FIG. 1.

In one aspect, the step of inserting bone fusion material 400 into the internal passage 120 of the screw 100 comprises inserting bone fusion material into the lumen and removing the lumen. As one skilled in the art can appreciate, bone fusion material can continually be inserted as the lumen is being removed in order to completely fill the internal passage.

The method can also comprise the step of placing a stylet (not shown) in the internal passageway over the guide wire to keep the internal passageway clear of debris, and removing the stylet prior to injecting the bone fusion material.

In one exemplified aspect, the method further comprises the step of injecting a radio-opaque substance into the internal passageway such that it secretes from the at least one shank aperture 152 prior to the injection of the bone fusion material in order to assess the status of the bone joint into which the bone fusion material is to be injected.

In a similar aspect, the method can comprise using the system to repair a damaged vertebra by driving the screw into the vertebra and across a cracked or damaged portion to stabilize the bone. In this aspect, it may be helpful to have a lag portion of the screw, rather than having substantially the entire shank threaded as illustrated in the figures herein. In one aspect, the threads substantially adjacent the tip portion can differ in pitch than the threads substantially adjacent the head. In a similar aspect, the method can also comprise driving the screw across a non-vertebral cracked or damaged bone.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed herein above, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

I claim:

1. A method for stabilization across a bone joint in the spine, comprising:
   providing a screw comprising:
      an elongate shank defining an internal longitudinal passage therethrough the shank, and having an external threaded surface, and a tapered distal end defining a tip aperture in communication with the internal longitudinal passage, the external threaded surface defining at least one substantially longitudinal groove and at least one shank aperture in communication with the internal longitudinal passage and the substantially longitudinal groove; and
      a head configured for engagement with a portion of an insertion tool and positioned at a proximal end of the elongate shank, the head defining a head aperture in communication with the internal longitudinal passage;
   providing an insertion tool comprising:
      an elongate tube having a longitudinal length and a tube distal end configured to mate with a portion of the head of the screw;
      a lumen extending substantially the longitudinal length of the elongate tube and extending from the tube distal end of the elongate tube, wherein a portion of the lumen is positionable within the internal longitudinal passage of the bone screw, wherein when the lumen is positioned within the internal passage the lumen substantially prevents communication between the internal longitudinal passage and the at least one shank aperture; and a drive rod disposed within the tube having a rod distal end configured to mate with and drive the screw, the drive rod defining a longitudinal drive rod passageway, wherein the rod is selectively removable from the elongate tube;

positioning the lumen of the insertion tool within the internal longitudinal passage, wherein when the lumen is positioned within the internal passage the lumen substantially prevents communication between the internal longitudinal passage and the at least one shank aperture;

accessing a desired motion segment;

inserting a guide wire along a selected trajectory to cross a bone joint of the desired motion segment;

placing the screw over the guide wire and driving it across the bone joint;

removing the guide wire; and injecting bone fusion material into the internal passageway and removing the lumen to enable the bone fusion material to secrete from the at least one shank aperture.

2. The method of claim 1, wherein the bone fusion material secretes from the at least on shank aperture and is placed in proximity to the bone of a superior facet of a first vertebral bone and the inferior facet of a second adjacent vertebral bone.

3. The method of claim 1, wherein the bone fusion material exits the internal passageway along the substantially longitudinal groove.

4. The method of claim 1, wherein the bone joint is a facet joint.

5. The method of claim 1, wherein the bone joint is in a lumbar region of the spine.

6. The method of claim 1, wherein the guide wire is a Kirschner wire.

7. The method of claim 1, further comprising the step of passing a drill over the guide wire and pre-drilling a desired area of the bone joint to facilitate the screw prior to the step of placing the screw over the guide wire and driving it across the bone joint.

8. The method of claim 1, further comprising the step of placing a stylet in the internal passageway over the guide wire to keep the internal passageway clear of debris, and removing the stylet prior to injecting the bone fusion material.

9. The method of claim 1, wherein the bone fusion material is selected from the group consisting of autologous bone, allograft bone, bone substitute, osteoinductive agent, and bone cement.

10. The method of claim 1, further comprising the step of injecting a radio-opaque substance into the internal passageway such that it secretes from the at least one shank aperture prior to the injection of the bone fusion material to assess the bone joint into which the bone fusion material is to be injected.

11. A system for bone fixation, comprising:

a bone screw comprising:

an elongate shank defining an internal longitudinal passage, and having an external threaded surface, and a tapered distal end defining a tip aperture in communication with the internal longitudinal passage, the external threaded surface defining at least one substantially longitudinal groove and at least one shank aperture in communication with the internal longitudinal passage and the substantially longitudinal groove; and a head positioned at a proximal end of the elongate shank, the head defining a head aperture in communication with the internal longitudinal passage; and an insertion tool comprising:

an elongate tube having a longitudinal length and a tube distal end configured to mate with a portion of the head of the screw;

a lumen extending substantially the longitudinal length of the elongate tube and extending from the tube distal end of the elongate tube, wherein a portion of the lumen is positionable within the internal longitudinal passage of the bone screw, wherein when the lumen is positioned within the internal passage the lumen substantially prevents communication between the internal longitudinal passage and the at least one shank aperture; and a drive rod disposed within the tube having a rod distal end configured to mate with and drive the screw, the drive rod defining a longitudinal drive rod passageway, wherein the rod is selectively removable from the elongate tube.

12. The system of claim 11, wherein the substantially longitudinal groove comprises a plurality of spaced substantially longitudinal grooves.

13. The system of claim 12, wherein the plurality of substantially longitudinal grooves are substantially parallel to a longitudinal axis of the elongate shank.

14. The system of claim 12, wherein the plurality of substantially longitudinal grooves are positioned at an acute angle relative to a longitudinal axis of the elongate shank.

15. The system of claim 11, wherein the at least one shank aperture comprises a plurality of shank apertures.

16. The system of claim 11, wherein the at least one shank aperture is elongated along the groove.

17. The system of claim 11, wherein a portion of the head is keyed for complimentary receipt of the rod distal end.

18. The system of claim 11, wherein the drive rod passageway is sized for complimentary receipt of a guide wire.

* * * * *